(12) United States Patent
Burbank

(10) Patent No.: US 11,717,290 B2
(45) Date of Patent: Aug. 8, 2023

(54) END EFFECTOR WITH REDUNDANT CLOSING MECHANISMS

(71) Applicant: Intuitive Surgical Operations, Inc., Sunnyvale, CA (US)

(72) Inventor: William A. Burbank, Sandy Hook, CT (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 92 days.

(21) Appl. No.: 17/130,464

(22) Filed: Dec. 22, 2020

(65) Prior Publication Data

US 2021/0106330 A1     Apr. 15, 2021

Related U.S. Application Data

(60) Continuation of application No. 16/141,663, filed on Sep. 25, 2018, now Pat. No. 10,898,188, which is a
(Continued)

(51) Int. Cl.
*A61B 17/072*     (2006.01)
*A61B 34/30*       (2016.01)
(Continued)

(52) U.S. Cl.
CPC ...... *A61B 17/072* (2013.01); *A61B 17/07207* (2013.01); *A61B 17/285* (2013.01);
(Continued)

(58) Field of Classification Search
CPC .............................. A61B 17/072; A61B 34/30
See application file for complete search history.

(56) References Cited

U.S. PATENT DOCUMENTS

| 61,581 A | 1/1867 | Taylor et al. |
| 76,819 A | 4/1868 | Ross et al. |

(Continued)

FOREIGN PATENT DOCUMENTS

| CN | 1457747 A | 11/2003 |
| CN | 1534213 A | 10/2004 |

(Continued)

OTHER PUBLICATIONS

Extended European Search Report for Application No. EP20187989.7 dated Dec. 4, 2020, 08 pages.

(Continued)

*Primary Examiner* — Nathaniel C Chukwurah
(74) *Attorney, Agent, or Firm* — Kilpatrick Townsend & Stockton LLP

(57) ABSTRACT

Surgical instruments operable to apply a grasping force to a tissue include a cable driven actuation mechanism. A surgical instrument includes an end effector and a first actuation mechanism. The end effector includes an end effector base, an articulated jaw pivotally coupled to the end effector base, and an opposing jaw. The first actuation mechanism includes a first pulley and a first cable segment. The first pulley is mounted for rotation relative to the end effector base. The first cable segment is interfaced with a sector of the first pulley. The first cable segment is coupled to the articulated jaw. The first actuation mechanism is operable to retract the first cable segment to cause the articulated jaw to apply a grasping force to a tissue disposed between the articulated jaw and the opposing jaw.

20 Claims, 14 Drawing Sheets

Related U.S. Application Data continuation of application No. 14/980,233, filed on Dec. 28, 2015, now Pat. No. 10,098,635, which is a continuation of application No. 14/519,908, filed on Oct. 21, 2014, now Pat. No. 9,226,761, which is a division of application No. 12/945,541, filed on Nov. 12, 2010, now Pat. No. 8,876,857.

(60) Provisional application No. 61/260,907, filed on Nov. 13, 2009.

(51) Int. Cl.
| | | |
|---|---|---|
| *A61B 34/00* | (2016.01) | |
| *A61B 50/10* | (2016.01) | |
| *A61B 50/13* | (2016.01) | |
| *A61B 50/15* | (2016.01) | |
| *A61B 34/37* | (2016.01) | |
| *A61B 17/29* | (2006.01) | |
| *A61B 17/285* | (2006.01) | |
| *A61B 17/32* | (2006.01) | |
| *A61B 17/00* | (2006.01) | |

(52) U.S. Cl.
CPC ...... *A61B 17/29* (2013.01); *A61B 17/320016* (2013.01); *A61B 34/30* (2016.02); *A61B 34/37* (2016.02); *A61B 34/71* (2016.02); *A61B 50/10* (2016.02); *A61B 50/13* (2016.02); *A61B 50/15* (2016.02); *A61B 2017/00398* (2013.01); *A61B 2017/00477* (2013.01); *A61B 2017/07214* (2013.01); *A61B 2017/2932* (2013.01); *A61B 2017/2933* (2013.01); *A61B 2017/2938* (2013.01); *A61B 2017/2946* (2013.01); *A61B 2017/2947* (2013.01); *A61B 2017/320052* (2013.01)

(56) References Cited

U.S. PATENT DOCUMENTS

| | | | |
|---|---|---|---|
| 1,665,241 | A | 4/1928 | Weiss |
| 2,067,286 | A | 1/1937 | Pearce |
| 2,297,457 | A | 9/1942 | Josef |
| 2,302,599 | A | 11/1942 | Burney |
| 2,687,025 | A | 8/1954 | Ernest |
| 3,017,755 | A | 1/1962 | Miller |
| 3,324,683 | A | 6/1967 | Schroter |
| 3,720,954 | A | 3/1973 | Czyryk |
| 3,747,368 | A | 7/1973 | Morin |
| 3,857,256 | A | 12/1974 | Girguis et al. |
| 3,906,747 | A | 9/1975 | Orain |
| 3,940,946 | A | 3/1976 | Andersen |
| 4,606,695 | A | 8/1986 | Lenz |
| 4,642,021 | A | 2/1987 | Kikuchi |
| 4,686,866 | A | 8/1987 | Rosheim |
| 4,790,225 | A | 12/1988 | Moody et al. |
| 4,799,817 | A | 1/1989 | Geisthoff |
| 4,892,300 | A | 1/1990 | Svyatsky |
| 4,911,033 | A | 3/1990 | Rosheim et al. |
| 4,969,533 | A | 11/1990 | Holm et al. |
| 5,062,761 | A | 11/1991 | Glachet |
| 5,069,569 | A | 12/1991 | Lieser |
| 5,101,681 | A | 4/1992 | Shpigel |
| 5,314,466 | A | 5/1994 | Stern et al. |
| 5,507,773 | A * | 4/1996 | Huitema ............ A61B 17/29 606/174 |
| 5,710,870 | A | 1/1998 | Ohm et al. |
| 5,740,699 | A | 4/1998 | Ballantyne et al. |
| 5,792,135 | A | 8/1998 | Madhani et al. |
| 5,797,900 | A | 8/1998 | Madhani et al. |
| 5,828,813 | A | 10/1998 | Ohm |
| 5,887,778 | A | 3/1999 | Maurer et al. |
| 5,954,259 | A | 9/1999 | Viola et al. |
| 6,010,054 | A | 1/2000 | Johnson et al. |
| 6,394,998 | B1 | 5/2002 | Wallace et al. |
| 6,676,684 | B1 | 1/2004 | Morley et al. |
| 6,685,698 | B2 | 2/2004 | Morley et al. |
| 6,699,235 | B2 | 3/2004 | Wallace et al. |
| 6,817,974 | B2 | 11/2004 | Cooper et al. |
| 6,860,860 | B2 | 3/2005 | Viola |
| 6,969,385 | B2 | 11/2005 | Moreyra |
| 7,066,926 | B2 | 6/2006 | Wallace et al. |
| 7,121,781 | B2 | 10/2006 | Sanchez |
| 7,320,700 | B2 | 1/2008 | Cooper et al. |
| 7,464,846 | B2 | 12/2008 | Shelton et al. |
| 7,485,127 | B2 | 2/2009 | Nistal |
| 7,641,671 | B2 * | 1/2010 | Crainich ............ A61B 17/12 606/205 |
| 7,708,758 | B2 | 5/2010 | Lee et al. |
| 7,918,230 | B2 | 4/2011 | Whitman et al. |
| 8,640,788 | B2 | 2/2014 | Dachs, II et al. |
| 8,852,174 | B2 | 10/2014 | Burbank |
| 8,876,857 | B2 | 11/2014 | Burbank |
| 9,101,381 | B2 | 8/2015 | Burbank et al. |
| 9,226,761 | B2 | 1/2016 | Burbank |
| 9,259,275 | B2 | 2/2016 | Burbank |
| 9,763,740 | B2 | 9/2017 | Dachs, II et al. |
| 10,045,823 | B2 | 8/2018 | Burbank |
| 10,098,635 | B2 | 10/2018 | Burbank |
| 10,206,748 | B2 | 2/2019 | Burbank |
| 10,292,767 | B2 | 5/2019 | Burbank et al. |
| 10,779,896 | B2 | 9/2020 | Dachs, II et al. |
| 10,835,331 | B2 | 11/2020 | Burbank |
| 11,083,458 | B2 | 8/2021 | Harris et al. |
| 11,291,447 | B2 | 4/2022 | Shelton, IV et al. |
| 11,304,696 | B2 | 4/2022 | Shelton, IV et al. |
| 11,304,768 | B2 | 4/2022 | Burbank |
| 11,317,917 | B2 | 5/2022 | Shelton, IV et al. |
| 11,357,572 | B2 | 6/2022 | Burbank et al. |
| 11,452,526 | B2 | 9/2022 | Ross et al. |
| 11,523,859 | B2 | 12/2022 | Shelton, IV et al. |
| 2001/0021859 | A1 | 9/2001 | Kawai et al. |
| 2001/0023311 | A1 | 9/2001 | Snow |
| 2002/0120265 | A1 | 8/2002 | Fowler |
| 2002/0143346 | A1 | 10/2002 | McGuckin, Jr. et al. |
| 2002/0188299 | A1 | 12/2002 | Reiley et al. |
| 2003/0105478 | A1 | 6/2003 | Whitman et al. |
| 2003/0114851 | A1 | 6/2003 | Truckai et al. |
| 2003/0130677 | A1 | 7/2003 | Whitman et al. |
| 2003/0158576 | A1 | 8/2003 | Nagase et al. |
| 2003/0192391 | A1 | 10/2003 | Uematsu et al. |
| 2003/0216667 | A1 | 11/2003 | Viola |
| 2004/0011576 | A1 | 1/2004 | Taniguchi et al. |
| 2004/0018909 | A1 | 1/2004 | Hwa et al. |
| 2004/0193146 | A1 | 9/2004 | Lee et al. |
| 2004/0260334 | A1 | 12/2004 | Braun |
| 2005/0075664 | A1 | 4/2005 | Nagase et al. |
| 2005/0163560 | A1 | 7/2005 | Chene et al. |
| 2006/0048787 | A1 | 3/2006 | Manzo et al. |
| 2006/0074415 | A1 | 4/2006 | Scott et al. |
| 2006/0079884 | A1 | 4/2006 | Manzo et al. |
| 2006/0089202 | A1 | 4/2006 | Losi, Jr. |
| 2006/0111209 | A1 | 5/2006 | Hinman et al. |
| 2006/0111210 | A1 | 5/2006 | Hinman |
| 2006/0137888 | A1 | 6/2006 | Soika et al. |
| 2006/0199909 | A1 | 9/2006 | Ikeda et al. |
| 2007/0023477 | A1 | 2/2007 | Whitman et al. |
| 2007/0055219 | A1 | 3/2007 | Whitman et al. |
| 2007/0233052 | A1 | 10/2007 | Brock |
| 2008/0039256 | A1 | 2/2008 | Jinno et al. |
| 2008/0058776 | A1 | 3/2008 | Jo et al. |
| 2008/0177283 | A1 | 7/2008 | Lee et al. |
| 2008/0257935 | A1 | 10/2008 | Viola et al. |
| 2008/0271906 | A1 | 11/2008 | Walker |
| 2008/0312668 | A1 | 12/2008 | Grace |
| 2009/0047061 | A1 | 2/2009 | Chene et al. |
| 2009/0065549 | A1 | 3/2009 | Viola |
| 2009/0090764 | A1 | 4/2009 | Viola et al. |
| 2009/0112229 | A1 | 4/2009 | Omori et al. |
| 2009/0173178 | A1 | 7/2009 | Okazaki |
| 2009/0183887 | A1 | 7/2009 | Baber et al. |
| 2009/0192519 | A1 | 7/2009 | Omori |
| 2009/0198253 | A1 | 8/2009 | Omori |

(56) References Cited

U.S. PATENT DOCUMENTS

| | | |
|---|---|---|
| 2009/0264931 A1 | 10/2009 | Miller et al. |
| 2010/0011900 A1 | 1/2010 | Burbank et al. |
| 2010/0011901 A1 | 1/2010 | Burbank |
| 2010/0016852 A1 | 1/2010 | Manzo et al. |
| 2010/0016853 A1 | 1/2010 | Burbank |
| 2011/0118708 A1 | 5/2011 | Burbank et al. |
| 2011/0152879 A1 | 6/2011 | Williams et al. |
| 2018/0318015 A1 | 11/2018 | Burbank et al. |
| 2019/0021733 A1 | 1/2019 | Burbank et al. |
| 2019/0099231 A1 | 4/2019 | Bruehwiler et al. |
| 2019/0298453 A1 | 10/2019 | Burbank et al. |
| 2020/0382921 A1 | 12/2020 | Dachs, II et al. |
| 2021/0338332 A1 | 11/2021 | Burbank |

FOREIGN PATENT DOCUMENTS

| | | |
|---|---|---|
| CN | 101365391 A | 2/2009 |
| CN | 101495046 A | 7/2009 |
| EP | 0710089 B1 | 12/2001 |
| EP | 1782927 A2 | 5/2007 |
| EP | 1813200 A2 | 8/2007 |
| EP | 2036505 B1 | 11/2010 |
| EP | 2263568 A2 | 12/2010 |
| EP | 1585425 B1 | 8/2016 |
| FR | 38899 E | 8/1931 |
| FR | 1012165 A | 7/1952 |
| GB | 195353 A | 3/1924 |
| GB | 802506 A | 10/1958 |
| GB | 2294526 A | 5/1996 |
| JP | 58217823 A | 12/1983 |
| JP | H03501233 A | 3/1991 |
| JP | H07163574 A | 6/1995 |
| JP | 2000023996 A | 1/2000 |
| JP | 2001276091 A | 10/2001 |
| JP | 2002306496 A | 10/2002 |
| JP | 2005505309 A | 2/2005 |
| JP | 2006075376 A | 3/2006 |
| JP | 2007038003 A | 2/2007 |
| JP | 2007130471 A | 5/2007 |
| JP | 2007524451 A | 8/2007 |
| JP | 2008036219 A | 2/2008 |
| JP | 2009502352 A | 1/2009 |
| JP | 2009066400 A | 4/2009 |
| JP | 2009112538 A | 5/2009 |
| JP | 2009165504 A | 7/2009 |
| JP | 2009178230 A | 8/2009 |
| JP | 2009178506 A | 8/2009 |
| JP | 2010540041 A | 12/2010 |
| WO | WO-8902544 A1 | 3/1989 |
| WO | WO-9743942 A1 | 11/1997 |
| WO | WO-9743943 A1 | 11/1997 |
| WO | WO-03001987 A2 | 1/2003 |
| WO | WO-2006073581 A2 | 7/2006 |
| WO | WO-2006075153 A1 | 7/2006 |
| WO | WO-20071 20353 A2 | 10/2007 |
| WO | WO-2007146987 A2 | 12/2007 |
| WO | WO-2009039506 A1 | 3/2009 |
| WO | WO-2009126955 A2 | 10/2009 |
| WO | WO-2011060315 A2 | 5/2011 |

OTHER PUBLICATIONS

Communication Pursuant to Article 94(3) EPC dated Jul. 12, 2013 for European Application No. 10781556.5 filed Nov. 12, 2010.
Communication Pursuant to Article 94(3) EPC dated Dec. 20, 2013 for European Application No. 10779428.1 filed Nov. 12, 2010.
Extended European Search Report for Application No. EP19203804 dated Feb. 3, 2020, 7 pages.
Extended European Search Report for Application No. 12162263.3, dated Oct. 26, 2016. 7 pages.
Extended European Search Report for Application No. 12162273.2, dated Oct. 26, 2016, 7 pages.
Extended European Search Report for Application No. 13151922.5, dated Oct. 26, 2016, 7 pages.
Extended European Search Report for Application No. 18171951.9, dated Aug. 7, 2018, 7 pages.
Extended European Search Report for Application No. 18198026.9, dated Dec. 3, 2018, 8 pages.
Extended European Search Report for Application No. EP18170942.9, dated Aug. 6, 2018, 9 pages.
Extended European Search Report for Application No. EP19206336 dated Feb. 11, 2020, 9 pages.
Office Action dated Jul. 2, 2014 for Chinese Application No. 201080051475.3 filed Nov. 12, 2010.
Office Action dated May 2, 2014 for Japanese Application No. 2012539033 filed Nov. 12, 2010.
Office Action dated May 8, 2014 for Japanese Application No. 2012539037 filed Nov. 12, 2010.
Office Action dated Aug. 13, 2014 for Japanese Application No. 2012539035 filed Nov. 13, 2009.
Office Action dated Jun. 17, 2015 for Japanese Application No. 2013200054 filed Sep. 26, 2013, 10 pages.
Office Action dated Aug. 26, 2014 for Japanese Application No. 2013200054 filed Sep. 26, 2013.
Office Action dated Aug. 29, 2014 for Japanese Application No. 2013200053 filed Sep. 26, 2013.
Office Action dated May 6, 2014 for Chinese Application No. 201080051059.3 filed Nov. 12, 2010.
PCT/US10/56601 International Search Report and Written Opinion of the International Searching Authority, dated Jul. 6, 2011, 18 pages.
PCT/US10/56607 Invitation to Pay Additional Fees and Results of the Partial International Search, dated Mar. 21, 2011, 5 pages.
PCT/US10/56610 International Search Report and Written Opinion of the International Searching Authority, dated Feb. 18, 2011, 16 pages.
PCT/US2010/056607 International Search Report and Written Opinion of the International Searching Authority, dated Jun. 15, 2011, 20 pages.
Rosheim, Mark E., Chapter 5: "Pitch-Yaw-Roll Wrists," Robot Wrist Actuators, Wiley & Sons, New York, 1989, pp. 95-206.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Extended European Search Report for Application No. EP22170371.3, dated Jul. 29, 2022, 09 pages.

* cited by examiner

END EFFECTOR WITH REDUNDANT CLOSING MECHANISMS

CROSS-REFERENCES TO RELATED APPLICATIONS

The present application is a Continuation of U.S. patent application Ser. No. 16/141,663 filed Sep. 25, 2018 (Allowed); which is a Continuation of U.S. Ser. No. 14/980,233 filed Dec. 28, 112018112015 (now U.S. Pat. No. 10,098,635); which is a Continuation of U.S. Ser. No. 14/519,908 filed Oct. 21, 2014 (now U.S. Pat. No. 9,226,761); which is a Divisional of U.S. Ser. No. 12/945,541 filed Nov. 12, 2010 (now U.S. Pat. No. 8,876,857); which claims the benefit of U.S. Provisional Appln No. 61/260,907 filed Nov. 13, 2009; the disclosures of which are incorporated herein by reference in their entirety for all purposes.

This application is also related to co-assigned U.S. application Ser. No. 12/945,730 filed Nov. 12, 2010 (now U.S. Pat. No. 9,259,275); U.S. Ser. No. 12/945,740 filed Nov. 12, 2010; U.S. Ser. No. 12/945,748 filed Nov. 12, 2010 (now U.S. Pat. No. 8,852,174); and U.S. application Ser. No. 12/945,461 filed Nov. 12, 2010 (now U.S. Pat. No. 8,640,788); the full disclosures of which are also incorporated herein by reference in their entirety for all purposes.

BACKGROUND

Minimally invasive surgical techniques are aimed at reducing the amount of extraneous tissue that is damaged during diagnostic or surgical procedures, thereby reducing patient recovery time, discomfort, and deleterious side effects. As a consequence, the average length of a hospital stay for standard surgery may be shortened significantly using minimally invasive surgical techniques. Also, patient recovery times, patient discomfort, surgical side effects, and time away from work may also be reduced with minimally invasive surgery.

A common form of minimally invasive surgery is endoscopy, and a common form of endoscopy is laparoscopy, which is minimally invasive inspection and surgery inside the abdominal cavity. In standard laparoscopic surgery, a patient's abdomen is insufflated with gas, and cannula sleeves are passed through small (approximately one-half inch or less) incisions to provide entry ports for laparoscopic instruments.

Laparoscopic surgical instruments generally include an endoscope (e.g., laparoscope) for viewing the surgical field and tools for working at the surgical site. The working tools are typically similar to those used in conventional (open) surgery, except that the working end or end effector of each tool is separated from its handle by an extension tube (also known as, e.g., an instrument shaft or a main shaft). The end effector can include, for example, a clamp, grasper, scissor, stapler, cautery tool, linear cutter, or needle holder.

To perform surgical procedures, the surgeon passes working tools through cannula sleeves to an internal surgical site and manipulates them from outside the abdomen. The surgeon views the procedure by means of a monitor that displays an image of the surgical site taken from the endoscope. Similar endoscopic techniques are employed in, for example, arthroscopy, retroperitoneoscopy, pelviscopy, nephroscopy, cystoscopy, cisternoscopy, sinoscopy, hysteroscopy, urethroscopy, and the like.

Minimally invasive telesurgical robotic systems are being developed to increase a surgeon's dexterity when working on an internal surgical site, as well as to allow a surgeon to operate on a patient from a remote location (outside the sterile field). In a telesurgery system, the surgeon is often provided with an image of the surgical site at a control console. While viewing a three dimensional image of the surgical site on a suitable viewer or display, the surgeon performs the surgical procedures on the patient by manipulating master input or control devices of the control console. Each of the master input devices controls the motion of a servo-mechanically actuated/articulated surgical instrument. During the surgical procedure, the telesurgical system can provide mechanical actuation and control of a variety of surgical instruments or tools having end effectors that perform various functions for the surgeon, for example, holding or driving a needle, grasping a blood vessel, dissecting tissue, or the like, in response to manipulation of the master input devices.

Non-robotic linear clamping, cutting and stapling devices have been employed in many different surgical procedures. For example, such a device can be used to resect a cancerous or anomalous tissue from a gastro-intestinal tract. Unfortunately, many known surgical devices, including known linear clamping, cutting and stapling devices, have opposing jaws that may generate less than a desired clamping force, which may reduce the effectiveness of the surgical device. Alternative devices may provide sufficient mechanical advantage to generate a desired level of clamping force for applicable surgical procedures (e.g., tissue stapling), but may have an actuation response rate that is less than desirable for telesurgical tissue manipulation. Furthermore, swapping tools having such high force jaw actuation mechanisms may be more complex (and potentially more prone to glitches) than would be ideal.

Thus, there is believed to be a need for tools with improved end effectors. Improved end effectors that provide sufficient clamping force, provide a fast response/low force articulation mode, and are at least partially back-drivable may also be desirable. Such tools may be beneficial in surgical applications, particularly in minimally invasive surgical applications.

BRIEF SUMMARY

Improved end effectors, related tools, and related methods are provided. In many surgical applications, for example, many minimally invasive surgical applications, the size of a surgical tool end effector is substantially constrained by applicable space constraints. While such a size constraint mitigates in favor of the use of one actuation mechanism, in many embodiments, the disclosed end effectors use two independent mechanisms to articulate a jaw of the end effector. In many embodiments, a first actuation mechanism provides a fast response/low force mode that varies the position of the articulated jaw between a clamped configuration and an open configuration. In many embodiments, the first actuation mechanism is back-drivable. In many embodiments, a second actuation mechanism provides a high clamping force mode that has a first configuration where the articulated jaw is held in a clamped configuration and a second configuration where the articulated jaw is unconstrained by the second actuation mechanism. In many embodiments, the second actuation mechanism is non-back-drivable.

Such end effectors, tools, and methods provide a number of benefits, particularly with respect to minimally invasive surgical applications. For example, in many embodiments, the high clamping force articulation mode enables proper tissue compression and resists jaw motion, for example, during staple firing. In many embodiments, the fast response/low force mode is useful for manipulating tissue, is useful for finding a more optimum tissue purchase, and provides a more responsive articulation of the articulated jaw. In many embodiments, a back-drivable first actuation mechanism permits the articulated jaw to move upon heavy contact with patient tissue, which may help to avoid injuring the patient tissue, and/or permits the articulated jaw to close upon contact with a cannula sleeve, which may aid in the removal of the surgical tool from the patient. Additionally, the disclosed end effectors may provide for improved tissue gap and/or tissue compression sensing because the redundant actuation mechanisms may provide additional feedback data for analysis and, in many embodiments, the first actuation mechanism can be made to function efficiently with low frictional losses, which may improve sensing capability. While the various embodiments disclosed herein are primarily described with regard to surgical applications, these surgical applications are merely example applications, and the disclosed end effectors, tools, and methods can be used in other suitable applications, both inside and outside a human body, as well as in non-surgical applications.

In a first aspect, a minimally invasive surgical method is provided. The method includes introducing a jaw of a tool to an internal surgical site within a patient through a minimally invasive aperture or natural orifice, manipulating tissue at the internal surgical site with a grasping force by articulating the jaw with a first actuation mechanism, and treating a target tissue at the internal surgical site using a clamping force by articulating the jaw of the tool with a second actuation mechanism. The first and second actuation mechanisms extend along a shaft from outside the patient to the jaw. The clamping force is greater than the grasping force.

In many embodiments, the first actuation mechanism comprises cable segments and the second actuation mechanism comprises a drive shaft. In many embodiments, the manipulation of the tissue is performed by closing the jaw using tension in a first cable segment and by opening the jaw using tension in a second cable segment. In many embodiments, the treatment of the tissue is performed by closing the jaw using a rotation of the drive shaft within the shaft of the tool. In many embodiments, the second actuation mechanism back-drives the first mechanism such that articulation of the second actuation mechanism to close the jaw will drive the cable segments toward a closed jaw configuration and articulation of the second actuation mechanism toward an open jaw configuration will not back-drive the first mechanism or open the jaw if the cable segments remain in a closed jaw configuration.

In another aspect, a surgical tool is provided. The tool includes an elongate shaft having a proximal end and a distal end, a tool body disposed at the distal end of the shaft, a jaw movable relative to the tool body between a clamped configuration and an open configuration, a first actuation mechanism coupled with the jaw, and a second actuation mechanism coupled with the jaw. The first actuation mechanism is operable to vary the position of the jaw relative to the tool body between the clamped configuration and the open configuration. The second actuation mechanism has a first configuration in which the jaw is held in the clamped configuration and a second configuration in which the position of the jaw relative to the tool body is unconstrained by the second actuation mechanism.

The first actuation mechanism can include one or more additional components and/or have one or more additional characteristics. For example, in many embodiments, the first actuation mechanism is back-drivable. In many embodiments, the first actuation mechanism includes cables. In many embodiments, a pulling movement of a first cable segment of the first actuation mechanism moves the jaw towards the open configuration and a pulling movement of a second cable segment of the first actuation mechanism moves the jaw towards the clamped configuration. The first actuation mechanism can include a first linkage coupling the first cable segment with the jaw and the tool body. The first actuation mechanism can include a second linkage coupling the second cable segment with the jaw and the tool body.

The second actuation mechanism can include one or more additional components and/or have one or more additional characteristics. For example, in many embodiments, the second actuation mechanism is non-back-drivable. The second actuation mechanism can be operable to produce a clamping force between the jaw and the tool body of at least 20 lbs. In many embodiments, the second actuation mechanism includes a leadscrew. The second actuation mechanism can include a leadscrew driven cam operatively coupled with the leadscrew and the jaw can include an interfacing cam surface for contact with the leadscrew driven cam.

The surgical tool can include one or more additional components. For example, the surgical tool can further include an actuated device. For example, the actuated device can be a cutting device, a stapling device, or a cutting and stapling device.

In another aspect, a robotic tool is provided for mounting on a manipulator having a first drive. The robotic tool includes a proximal tool chassis releasably mountable to the manipulator; a drive motor coupled with the tool chassis and disposed adjacent the tool chassis; a distal end effector comprising a movable jaw; an instrument shaft having a proximal end adjacent the chassis, and a distal end adjacent the end effector; a first actuation mechanism coupling the first drive to the end effector when the chassis is mounted to the manipulator so as to articulate the end effector between an open configuration and a clamped configuration; and a second actuation mechanism coupling the drive motor to the end effector so as to articulate the end effector into the clamped configuration from the open configuration.

The first actuation mechanism can include one or more additional components and/or have one or more additional characteristics. For example, in many embodiments, the first actuation mechanism is back-drivable. The first actuation mechanism can include cables extending from the chassis distally within a bore of the instrument shaft operatively coupling the end effector to the first drive.

The second actuation mechanism can include one or more additional components and/or have one or more additional characteristics. For example, in many embodiments, the second actuation mechanism is non-back-drivable. The second actuation mechanism can include a leadscrew driven cam. The second actuation mechanism can have a first configuration where the jaw is held in the clamped configuration and a second configuration where the position of the jaw relative to the tool body is unconstrained by the second actuation mechanism. The second actuation mechanism can include a drive shaft mounted for rotation within a bore of the instrument shaft and operatively coupling the end effector to the drive motor.

In another aspect, a surgical instrument is provided. The surgical instrument includes an end effector comprising a movable jaw, a first jaw actuation mechanism coupled to the movable jaw, and a second jaw actuation mechanism coupled to the moveable jaw. The first jaw actuation mechanism moves the jaw from an open position to a closed position independently of the second jaw actuation mechanism. The second jaw actuation mechanism moves the jaw from the open position to the closed position independently of the first jaw actuation mechanism.

The second jaw mechanism can constrain the range of motion in which the first actuation mechanism can move the jaw. For example, the second actuation mechanism can have a first configuration in which the movable jaw is held in a clamped position and in which the first actuation mechanism is prevented from moving the movable jaw.

The first actuation mechanism can provide a fast response/low force articulation mode, and the second actuation mechanism can provide a high clamping force mode. For example, in many embodiments, the maximum clamping force of the movable jaw provided by the second actuation mechanism is larger than a maximum clamping force provided by the first actuation mechanism.

The first and second actuation mechanisms can employ different force transmission mechanisms. For example, a force used by the first jaw actuation mechanism to move the jaw from the open to the close position can include a linear force, and a force used by the second jaw actuation mechanism to move the jaw from the open to the closed position can include a torque. In many embodiments, the first jaw actuation mechanism includes a cable-driven mechanism. In many embodiments, the second jaw actuation mechanism includes a leadscrew-driven mechanism.

For a fuller understanding of the nature and advantages of the present invention, reference should be made to the ensuing detailed description and accompanying drawings. Other aspects, objects and advantages of the invention will be apparent from the drawings and detailed description that follows.

DETAILED DESCRIPTION

Improved end effectors, related tools, and related methods are provided. In many embodiments, the disclosed end effectors use two independent mechanisms to articulate a jaw of the end effector. In many embodiments, a first actuation mechanisms provides a fast response/low force mode that varies the position of the articulated jaw between a clamped configuration and an open configuration. In many embodiments, the first actuation mechanism is back-drivable. The first actuation mechanism can be designed to provide, for example, 5 lbs of clamping force at the tip of the articulated jaw of the end effector. In many embodiments, a second actuation mechanism provides a high clamping force mode that has a first configuration where the articulated jaw is held in a clamped configuration and a second configuration where the articulated jaw is unconstrained by the second actuation mechanism. In many embodiments, the second actuation mechanism is non-back-drivable. In many embodiments, the second actuation mechanism converts a relatively weak force or torque (but with large displacement available) to a relatively high torque rotating the jaw of the end effector. The second actuation mechanism can be designed to provide, for example, 50 pounds of clamping force at the tip of the articulated jaw of the end effector. The disclosed end effectors, tools, and methods can be used in a variety of applications, and may be particularly beneficial when used in minimally invasive surgery applications. While the various embodiments disclosed herein are primarily described with regard to surgical applications, these surgical applications are merely example applications, and the disclosed end effectors, tools, and methods can be used in other suitable applications, both inside and outside a human body, as well as in non-surgical applications.

Minimally Invasive Robotic Surgery

Figure 1:
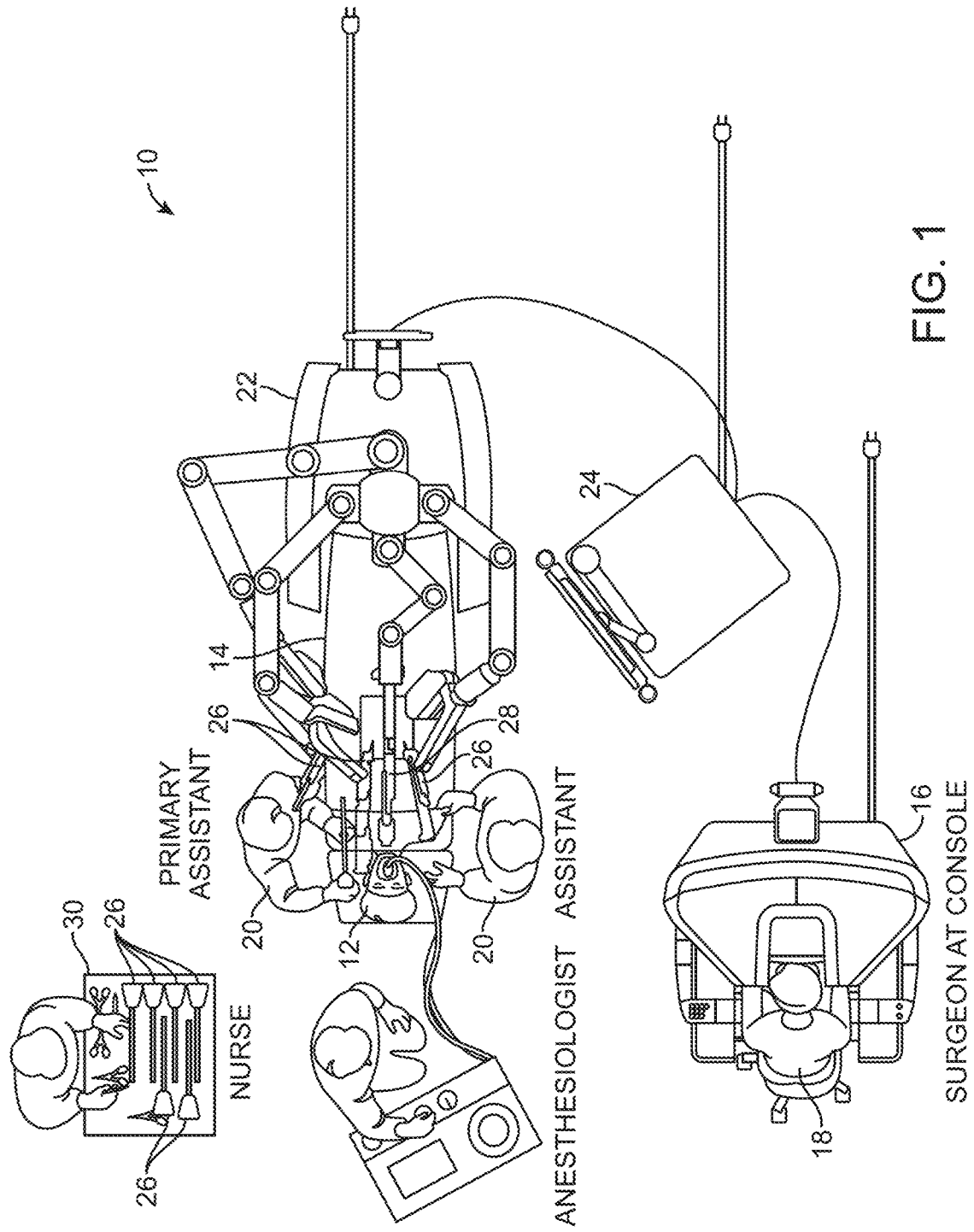
FIG. 1 is a plan view of a minimally invasive robotic surgery system being used to perform a surgery, in accordance with many embodiments.

Referring now to the drawings, in which like reference numerals represent like parts throughout the several views, FIG. 1 is a plan view illustration of a Minimally Invasive Robotic Surgical (MIRS) system 10, typically used for performing a minimally invasive diagnostic or surgical procedure on a Patient 12 who is lying down on an Operating table 14. The system can include a Surgeon's Console 16 for use by a Surgeon 18 during the procedure. One or more Assistants 20 may also participate in the procedure. The MIRS system 10 can further include a Patient Side Cart 22 (surgical robot), and an Electronics Cart 24. The Patient Side Cart 22 can manipulate at least one removably coupled tool assembly 26 (hereinafter simply referred to as a "tool") through a minimally invasive incision in the body of the Patient 12 while the Surgeon 18 views the surgical site through the Console 16. An image of the surgical site can be obtained by an endoscope 28, such as a stereoscopic endoscope, which can be manipulated by the Patient Side Cart 22 so as to orient the endoscope 28. The Electronics Cart 24 can be used to process the images of the surgical site for subsequent display to the Surgeon 18 through the Surgeon's Console 16. The number of surgical tools 26 used at one time will generally depend on the diagnostic or surgical procedure and the space constraints within the operating room among other factors. If it is necessary to change one or more of the tools 26 being used during a procedure, an Assistant 20 may remove the tool 26 from the Patient Side Cart 22, and replace it with another tool 26 from a tray 30 in the operating room.

Figure 2:
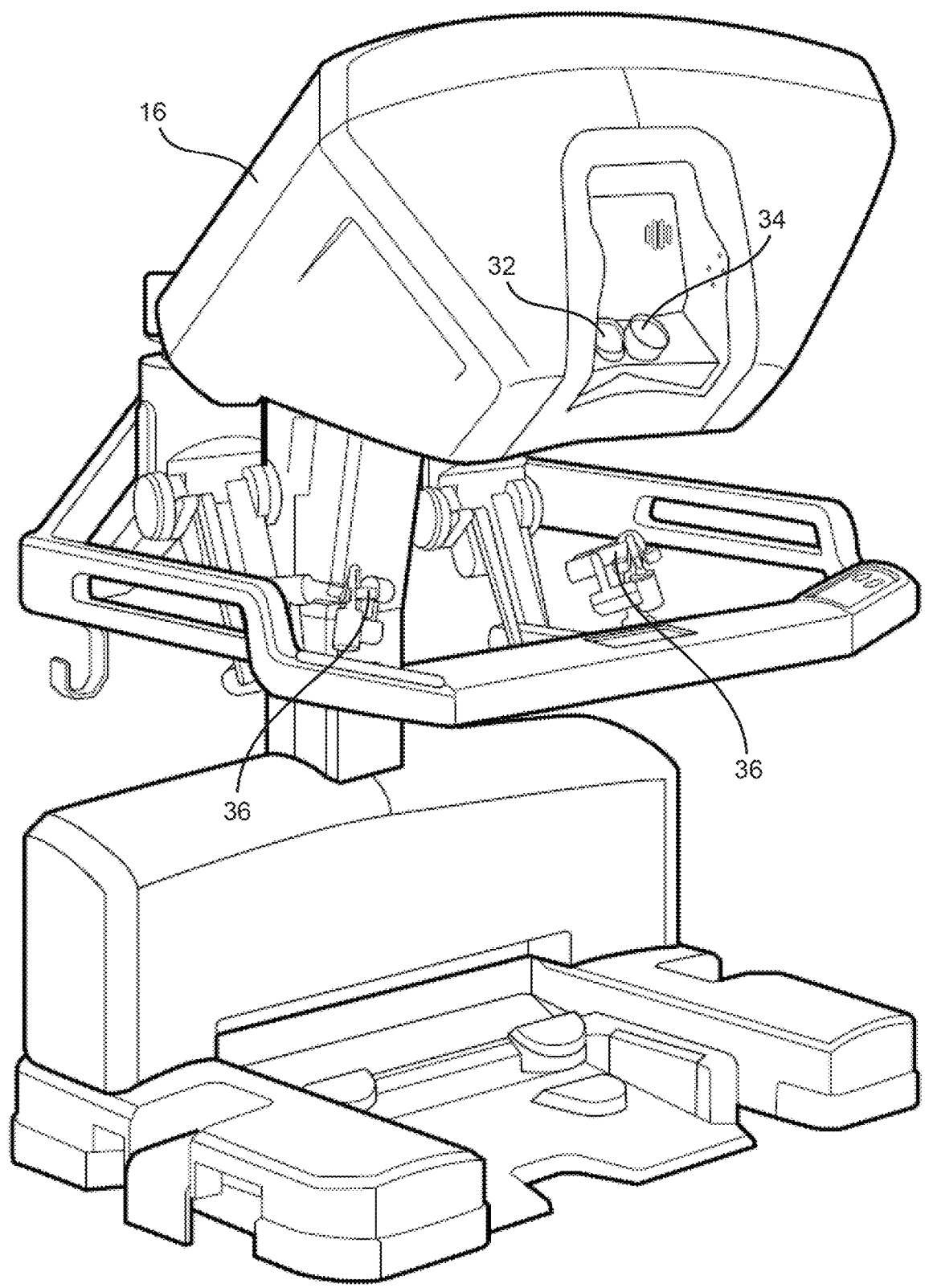
FIG. 2 is a perspective view of a surgeon's control console for a robotic surgery system, in accordance with many embodiments.

FIG. 2 is a perspective view of the Surgeon's Console 16. The Surgeon's Console 16 includes a left eye display 32 and a right eye display 34 for presenting the Surgeon 18 with a coordinated stereo view of the surgical site that enables depth perception. The Console 16 further includes one or more input control devices 36, which in turn cause the Patient Side Cart 22 (shown in FIG. 1) to manipulate one or more tools. The input control devices 36 will provide the same degrees of freedom as their associated tools 26 (shown in FIG. 1) so as to provide the Surgeon with telepresence, or the perception that the input control devices 36 are integral with the tools 26 so that the Surgeon has a strong sense of directly controlling the tools 26. To this end, position, force, and tactile feedback sensors (not shown) may be employed to transmit position, force, and tactile sensations from the tools 26 back to the Surgeon's hands through the input control devices 36.

The Surgeon's Console 16 is usually located in the same room as the patient so that the Surgeon may directly monitor the procedure, be physically present if necessary, and speak to an Assistant directly rather than over the telephone or other communication medium. However, the Surgeon can be located in a different room, a completely different building, or other remote location from the Patient allowing for remote surgical procedures (i.e., operating from outside the sterile field).

Figure 3:
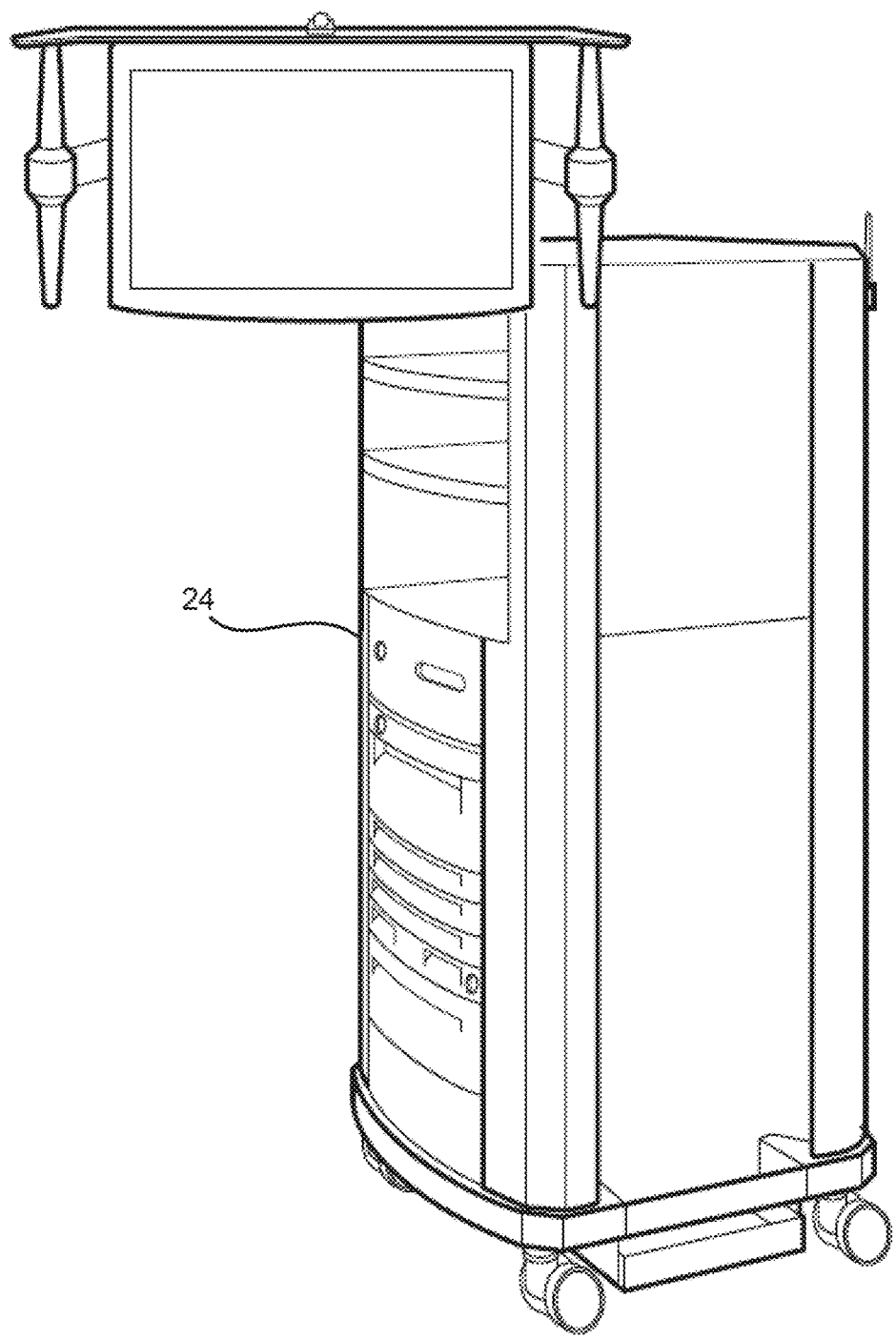
FIG. 3 is a perspective view of a robotic surgery system electronics cart, in accordance with many embodiments.

FIG. 3 is a perspective view of the Electronics Cart 24. The Electronics Cart 24 can be coupled with the endoscope 28 and can include a processor to process captured images for subsequent display, such as to a Surgeon on the Surgeon's Console, or on any other suitable display located locally and/or remotely. For example, where a stereoscopic endoscope is used, the Electronics Cart 24 can process the captured images so as to present the Surgeon with coordinated stereo images of the surgical site. Such coordination can include alignment between the opposing images and can include adjusting the stereo working distance of the stereoscopic endoscope. As another example, image processing can include the use of previously determined camera calibration parameters so as to compensate for imaging errors of the image capture device, such as optical aberrations.

Figure 4:
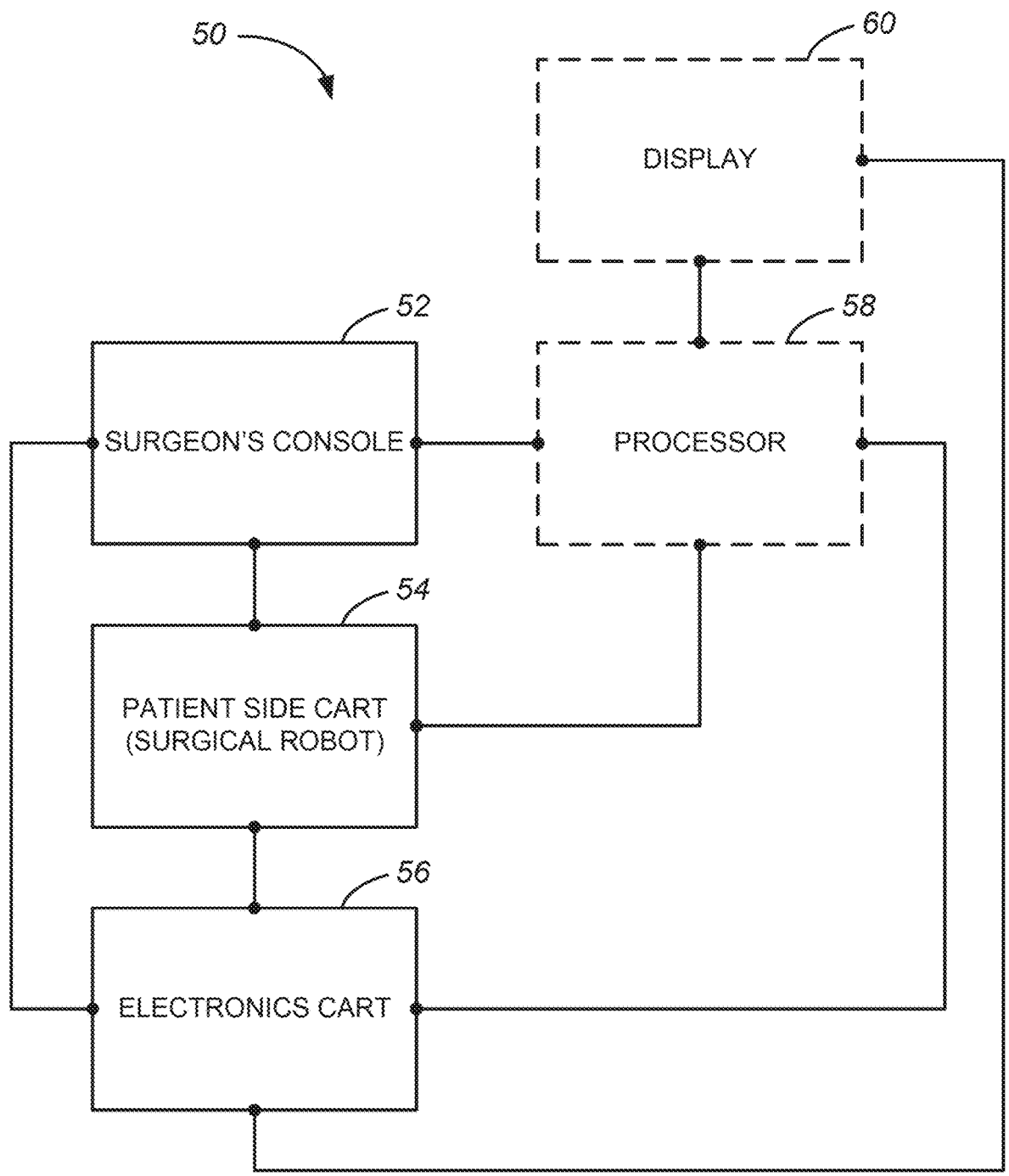
FIG. 4 diagrammatically illustrates a robotic surgery system, in accordance with many embodiments.

FIG. 4 diagrammatically illustrates a robotic surgery system 50 (such as MIRS system 10 of FIG. 1). As discussed above, a Surgeon's Console 52 (such as Surgeon's Console 16 in FIG. 1) can be used by a Surgeon to control a Patient Side Cart (Surgical Robot) 54 (such as Patent Side Cart 22 in FIG. 1) during a minimally invasive procedure. The Patient Side Cart 54 can use an imaging device, such as a stereoscopic endoscope, to capture images of the procedure site and output the captured images to an Electronics Cart 56 (such as the Electronics Cart 24 in FIG. 1). As discussed above, the Electronics Cart 56 can process the captured images in a variety of ways prior to any subsequent display. For example, the Electronics Cart 56 can overlay the captured images with a virtual control panel interface prior to displaying the combined images to the Surgeon via the Surgeon's Console 52. The Patient Side Cart 54 can output the captured images for processing outside the Electronics Cart 56. For example, the Patient Side Cart 54 can output the captured images to a processor 58, which can be used to process the captured images. The images can also be processed by a combination the Electronics Cart 56 and the processor 58, which can be coupled together so as to process the captured images jointly, sequentially, and/or combinations thereof. One or more separate displays 60 can also be coupled with the processor 58 and/or the Electronics Cart 56 for local and/or remote display of images, such as images of the procedure site, or any other related images.

Figure 5B:
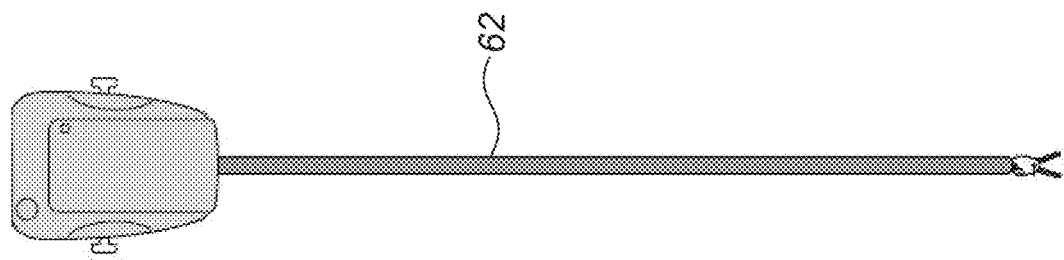
FIG. 5B is a front view of a robotic surgery tool.
Figure 5A:
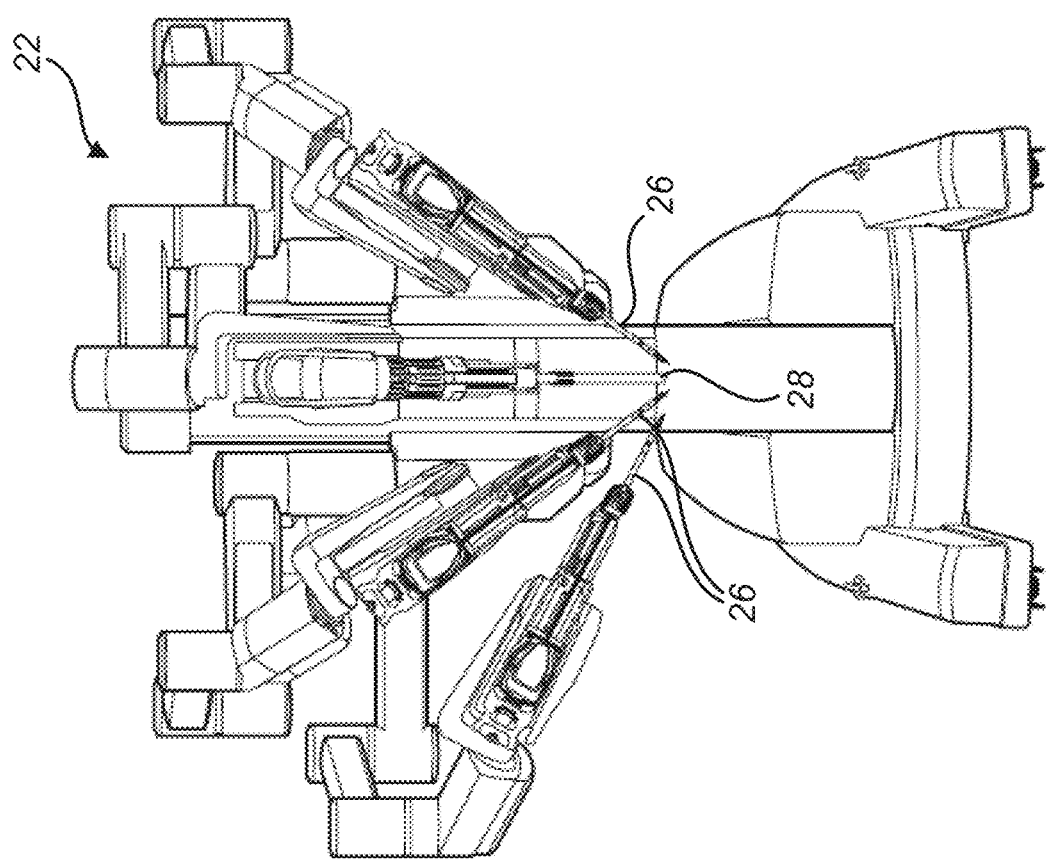
FIG. 5A is a front view of a patient side cart (surgical robot) of a robotic surgery system, in accordance with many embodiments.

FIGS. 5A and 5B show a Patient Side Cart 22 and a surgical tool 62, respectively. The surgical tool 62 is an example of the surgical tools 26. The Patient Side Cart 22 shown provides for the manipulation of three surgical tools 26 and an imaging device 28, such as a stereoscopic endoscope used for the capture of images of the site of the procedure. Manipulation is provided by robotic mechanisms having a number of robotic joints. The imaging device 28 and the surgical tools 26 can be positioned and manipulated through incisions in the patient so that a kinematic remote center is maintained at the incision so as to minimize the size of the incision. Images of the surgical site can include images of the distal ends of the surgical tools 26 when they are positioned within the field-of-view of the imaging device 28.

End Effector Jaw Articulation With Independent Actuation Mechanisms

In many embodiments, two independent actuation mechanisms are used to control the articulation of an articulated jaw of an end effector. A first actuation mechanism can be used to provide a fast response/low force mode, and a second actuation mechanism can be used to provide a high clamping force mode. In many embodiments, the first actuation mechanism used to provide the fast response/low force articulation mode is back-drivable. In many embodiments, the second actuation mechanism used to provide the high clamping force articulation mode is non-back-drivable. Such use of two independent actuation mechanisms may be beneficial in some surgical applications, for example, electrocautery sealing, stapling, etc., that may require multiple low force jaw placement clampings before a high force jaw clamping is used to carry out the surgical tool's task.

In many embodiments, the fast response/low force mode is provided by a cable actuation mechanism that includes a pair of pull cables. In many embodiments, a pulling motion of a first cable of the pair articulates the articulated jaw towards a closed (clamped) configuration and a pulling motion of a second cable of the pair articulates the articulated jaw towards an open configuration. In many embodiments, the cable actuation mechanism is back-drivable.

In many embodiments, the high clamping force mode is provided by a leadscrew actuation mechanism that includes a leadscrew driven cam. The driven cam interfaces with a mating cam surface on the articulated jaw so as to hold the articulated jaw in a clamped configuration when the leadscrew driven cam is at a first end of its range of motion. In addition, the driven cam does not constrain motion of the articulated jaw when the leadscrew driven cam is at a second end (opposite end) of its range of motion. In other words, the mating cam surfaces are arranged such that motion of the leadscrew driven cam in one direction will cause the articulated jaw to close, and motion of the leadscrew driven cam in the reverse direction will allow (but not force) the articulated jaw to open to a limit provided by the cam surfaces. In many embodiments, the leadscrew actuation mechanism is non-back-drivable.

Figure 6A:
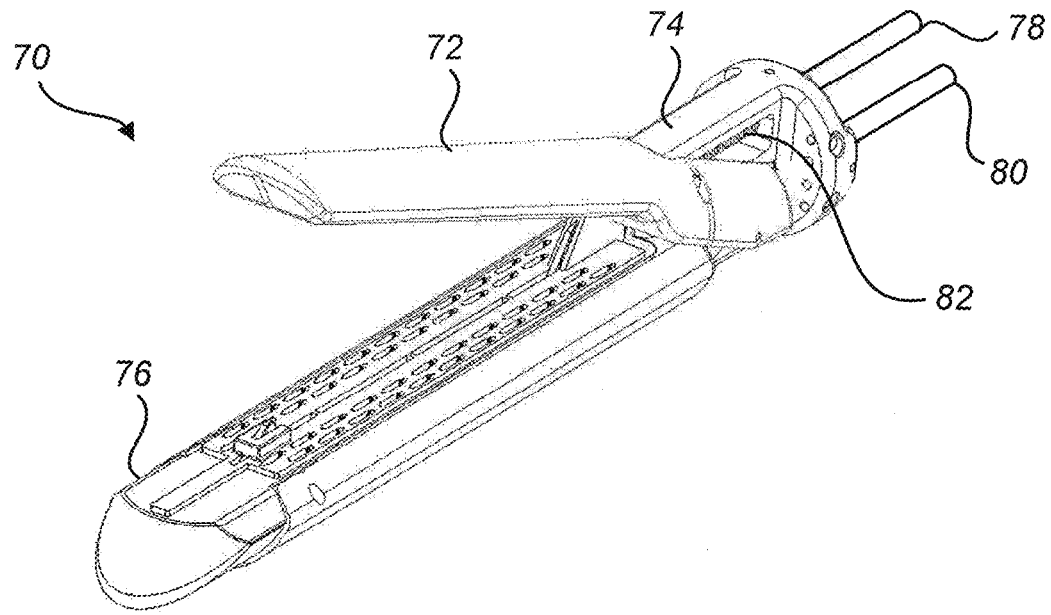
FIG. 6A is a perspective view of an end effector having an articulated jaw, in accordance with many embodiments.

FIG. 6A is a perspective view of an end effector 70 having a jaw 72 articulated by two independent actuation mechanisms, in accordance with many embodiments. The end effector 70 includes an end effector base 74, the articulated jaw 72, and a detachable stationary jaw 76. The end effector 70 is actuated via a first drive shaft 78, a second drive shaft 80, and two actuation cables (not shown). The first drive shaft 78 rotates a leadscrew 82 of a leadscrew actuation mechanism. The second drive shaft 80 rotates another leadscrew (not shown) of the detachable stationary jaw 76.

In many embodiments, the first drive shaft 78 and/or the second drive shaft 80 are driven by drive features located in a proximal tool chassis to which the end effector 70 is coupled with via an instrument shaft. In many embodiments, the proximal tool chassis is configured to be releasably mountable to a robotic tool manipulator. In many embodiments, the first drive shaft 78 and the second drive shaft 80 are actuated via respective drive features located in the proximal tool chassis. In many embodiments, such drive features are driven by motors that are located in the proximal tool chassis.

Figure 6B:
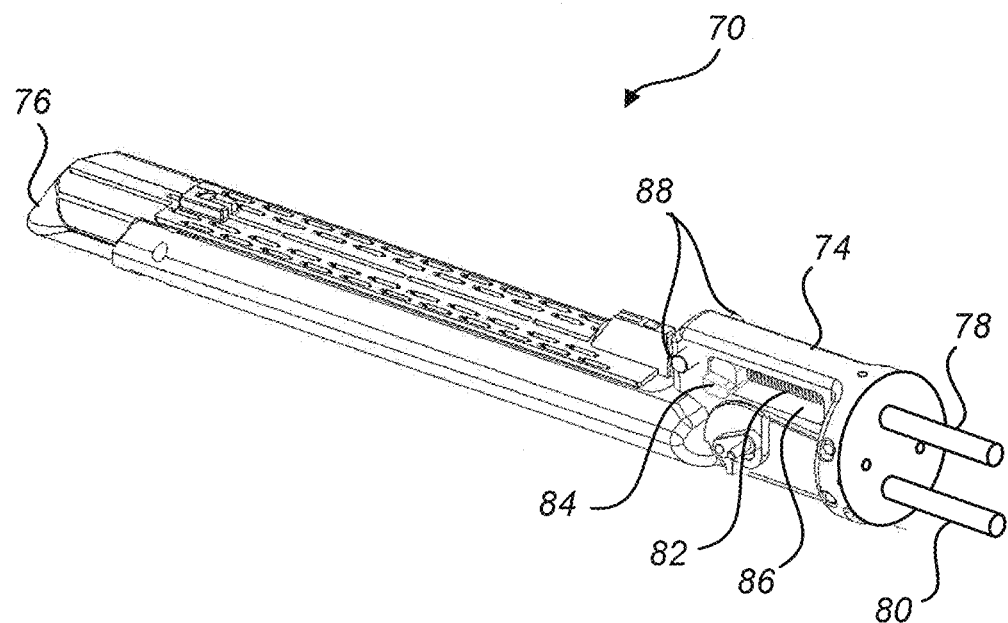
FIG. 6B is a perspective view of the end effector of FIG. 6A (with the articulated jaw removed to better illustrate leadscrew actuation mechanism components), in accordance with many embodiments.

FIG. 6B is a perspective view of the end effector 70 of FIG. 6A (with the articulated jaw 72 removed to better illustrate components of the leadscrew actuation mechanism), in accordance with many embodiments. The leadscrew 82 is mounted for rotation relative to the end effector base 74. A leadscrew driven cam 84 is coupled with the leadscrew 82 so that selective rotation of the leadscrew 82 can be used to selectively translate the leadscrew driven cam 84 along a cam slot 86 in the end effector base 74. The end effector 70 includes a pivot pin 88 that is used to rotationally couple the articulated jaw 72 with the end effector base 74.

Figure 7A:
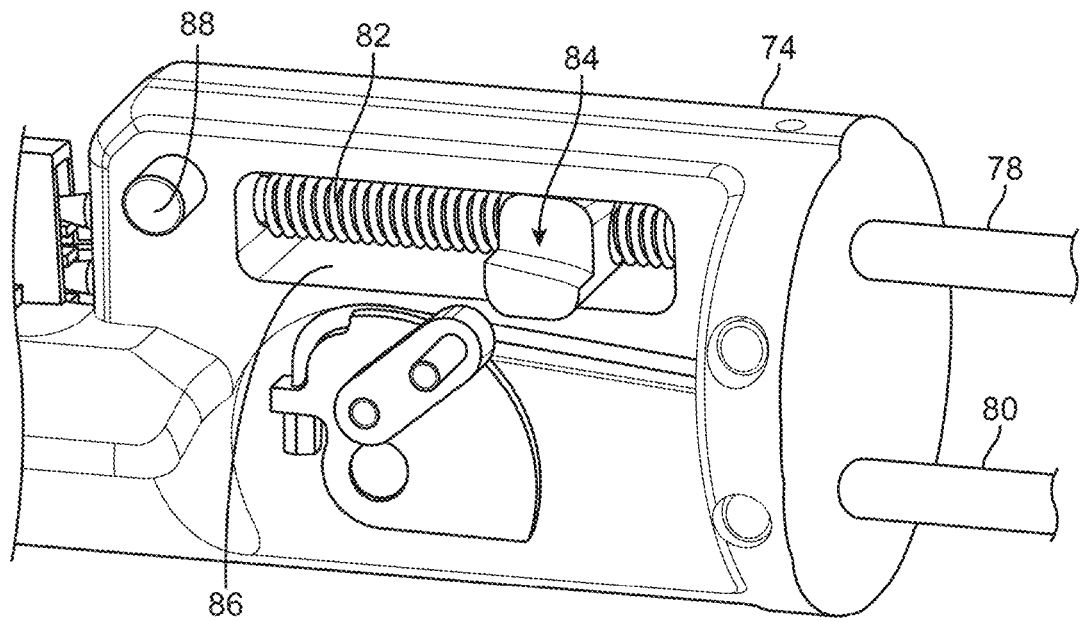
FIGS. 7A and 7B illustrate components of a leadscrew actuation mechanism, in accordance with many embodiments.
Figure 7B:
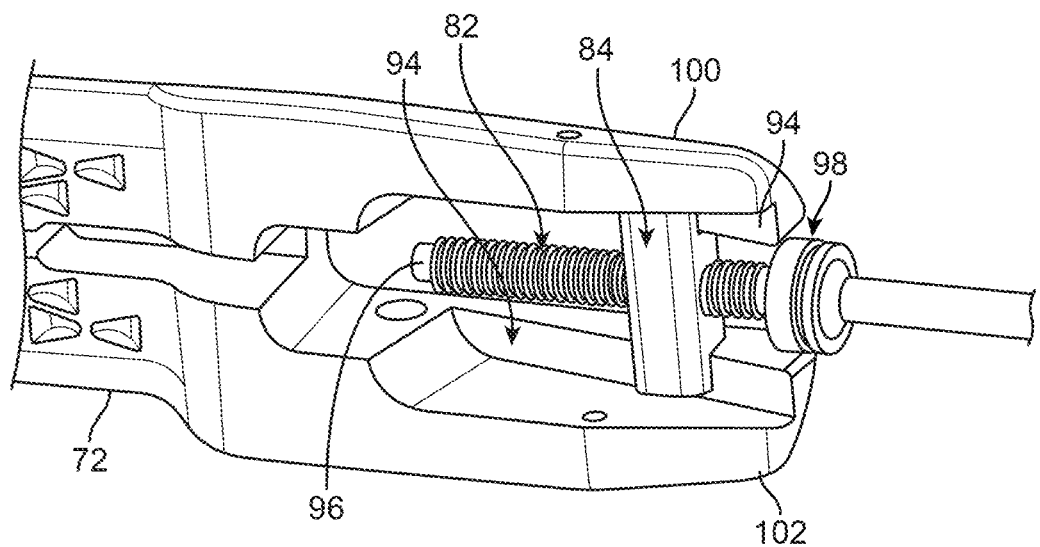
Figure 8A:
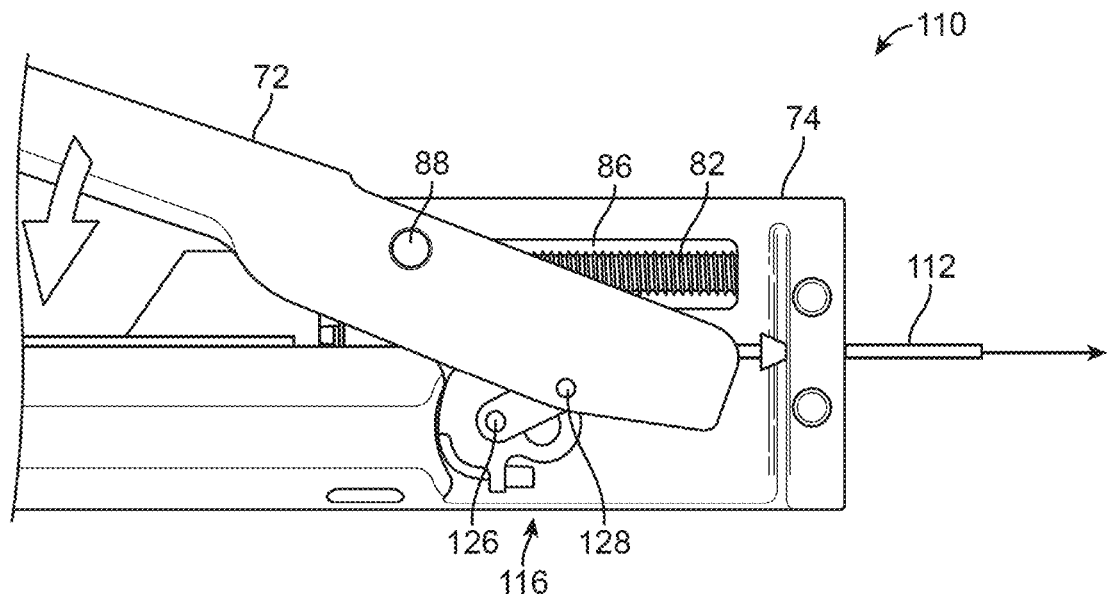
FIG. 8A illustrates components of a cable actuation mechanism, in accordance with many embodiments.
Figure 8B:
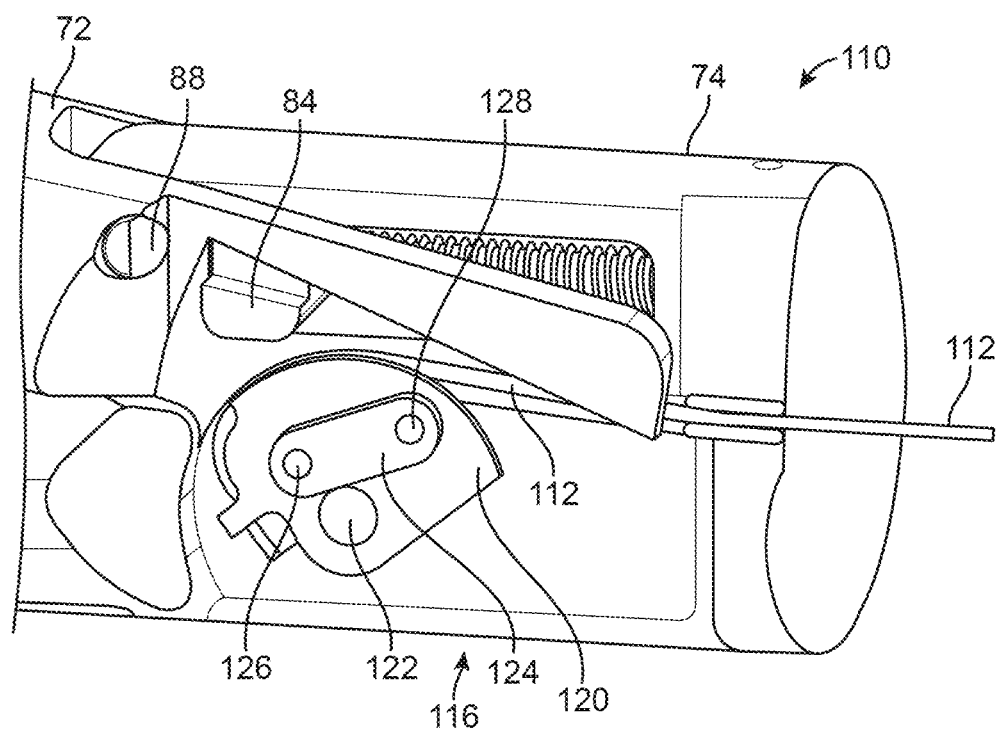
FIG. 8B is a perspective view of the end effector of FIG. 8A with a portion of the articulated jaw removed to show cable actuation mechanism components disposed behind the articulated jaw, in accordance with many embodiments.
Figure 8C:
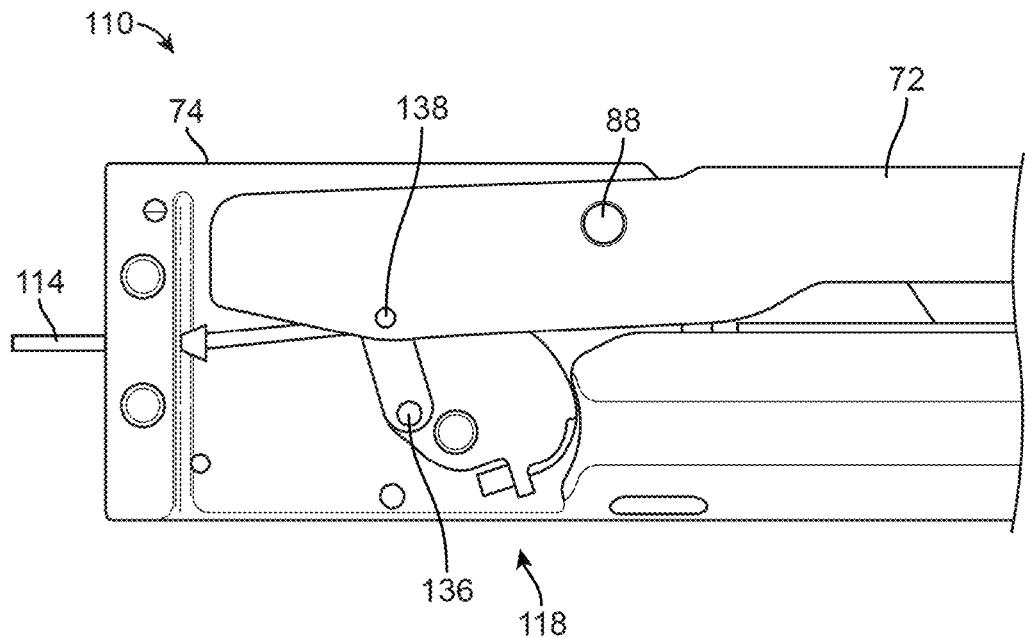
FIGS. 8C through 8F illustrate opposite side components of the cable actuation mechanism of FIG. 8A.
Figure 8D:
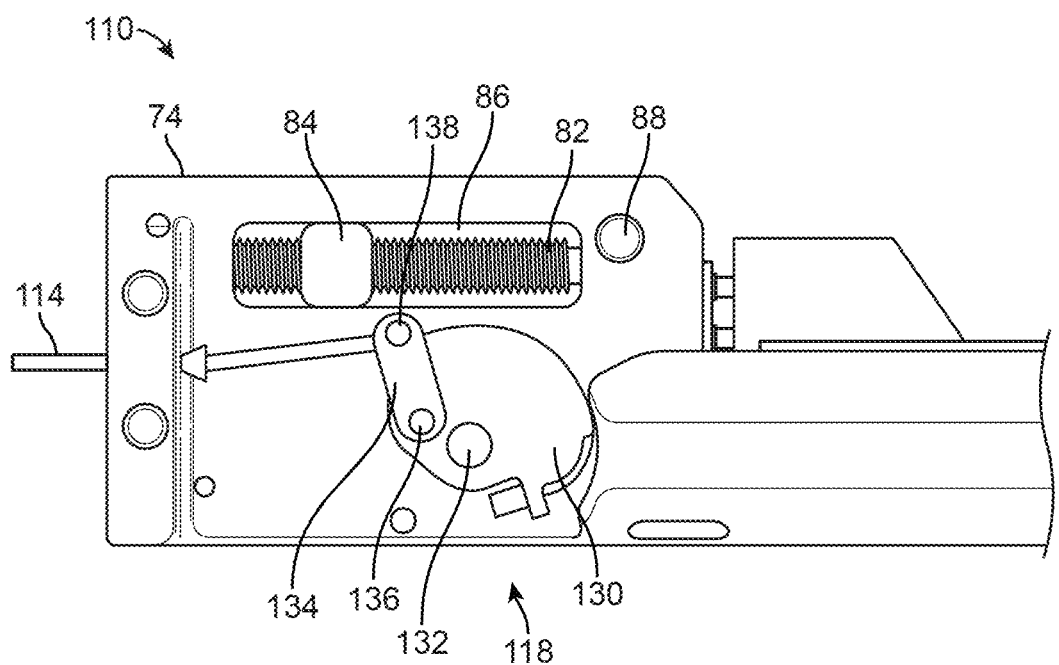
Figure 8E:
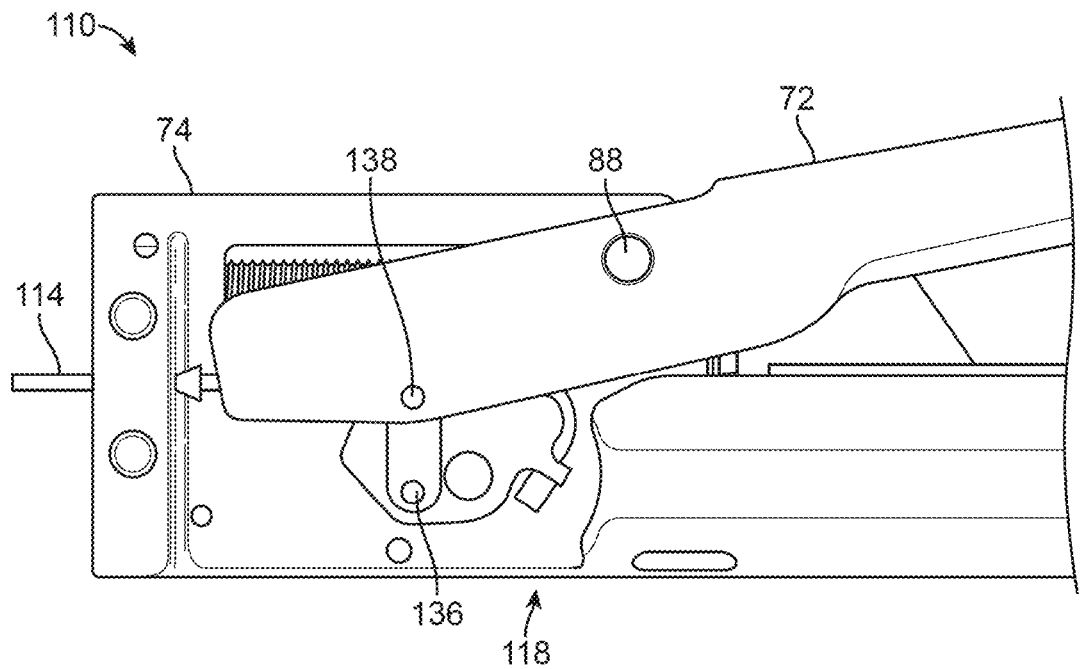
Figure 8F:
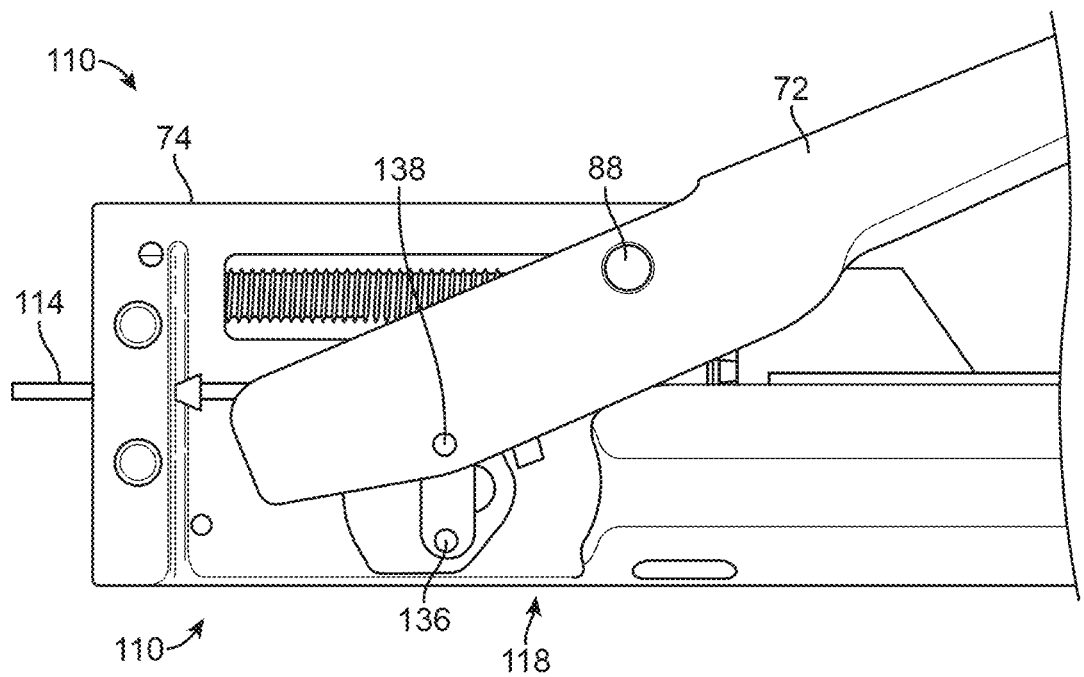

FIGS. 7A and 7B illustrate the leadscrew actuation mechanism of FIGS. 6A and 6B. The leadscrew 82 has a distal journal surface 96 and a proximal journal surface that interfaces with a proximal bearing 98. In many embodiments, the distal journal surface 96 is received within a cylindrical receptacle located at the distal end of the cam slot 86. Such a distal support for the leadscrew 82 can be configured to keep the leadscrew 82 from swinging excessively, and with relatively large clearance(s) between the distal journal surface 96 and the cylindrical receptacle. The proximal bearing 98 is supported by the end effector base 74 so as to support the proximal end of the leadscrew 82. The proximal bearing 98 can be a ball bearing, which may help to reduce friction and wear. A distal bearing (not shown) can be supported by the end effector base 74 so as to support the distal end of the leadscrew 82, and the distal bearing can be a ball bearing. The leadscrew driven cam 84 includes a threaded bore configured to mate with the external threads of the leadscrew 82. The leadscrew driven cam 84 includes top and bottom surfaces configured to interact with corresponding top and bottom surfaces of the cam slot 86. The interaction between leadscrew driven cam 84 and the cam slot 86 prevents the leadscrew driven cam 84 from rotating relative to the cam slot 86, which causes the leadscrew driven cam 84 to translate along the cam slot 86 in response to rotation of the leadscrew.

The articulated jaw 72 includes mating cam surfaces 94 that are configured so that the position of the leadscrew driven cam 84 along the cam slot 86 determines the extent to which the rotational motion of the articulated jaw 72 around the pivot pin 88 is constrained by the leadscrew driven cam 84. The articulated jaw 72 includes a first proximal side 100 and a second proximal side 102 that are separated by a central slot. The first and second proximal sides are disposed on opposing sides of the end effector base 74 when the articulated jaw 72 is coupled with the end effector base 74 via the pivot pin 88. Each of the first and second proximal sides 100, 102 includes a recessed area defining a mating cam surface 94 and providing clearance between the leadscrew driven cam 84 and the proximal sides 100, 102. When the leadscrew driven cam 84 is positioned at or near the proximal end of the cam slot 86 (near its position illustrated in FIGS. 7A and 7B), contact between the leadscrew driven cam 84 and the mating cam surfaces 94 of the articulated jaw 72 hold the articulated jaw in a clamped configuration. When the leadscrew driven cam 84 is positioned at the distal end of the cam slot 86, the rotational position of the articulated jaw around the pivot pin 88 is unconstrained by the leadscrew driven cam 84 for a range of rotational positions between a clamped configuration (where there is a gap between the leadscrew driven cam 84 and the mating cam surfaces 94 of the articulated jaw 72) and an open configuration (where there may or may not be a gap between the leadscrew driven cam 84 and the mating cam surfaces 94 of the articulated jaw 72). For positions of the leadscrew driven cam 84 in between the proximal and distal ends of the cam slot 86, the range of unconstrained motion can vary according to the cam surfaces used.

The use of a recess in each of the proximal sides 100, 102 to define the mating cam surfaces 94 of the articulated jaw 72 provides a number of benefits. For example, the use of recesses as opposed to traverse slots that extend through the proximal sides provides a continuous outside surface to the proximal sides 100, 102 of the articulated jaw, which is less likely to snag on patient tissue than would a traverse slot opening. The absence of traverse slots also helps to stiffen the proximal sides 100, 102 as compared to proximal sides with traverse slots, and therefore provides increased clamping stiffness. Such proximal sides 100, 102 may have increased stiffness in two planes, which may help maintain alignment of the articulated jaw 72 in the presences of external forces. Such increased stiffness in two planes may be beneficial in some surgical applications, for example, in tissue stapling where it is beneficial to maintain alignment between the staples and anvil pockets that form the staples. Further, the use of recesses instead of traverse slots also provides an actuation mechanism that is less likely to be jammed by extraneous material as compared to one having proximal sides with open traverse slots.

The leadscrew actuation mechanism can be configured to provide a desired clamping force between the articulated jaw and an opposing jaw of the end effector. For example, in many embodiments, the leadscrew actuation mechanism is configured to provide at least 20 lbs of clamping force at the tip of the articulated jaw 72 (approximately 2 inches from the pivot pin 88). In many embodiments, the leadscrew actuation mechanism is configured to provide at least 50 lbs of clamping force at the tip of the articulated jaw 72. In many embodiments, to produce 50 lbs of clamping force at the tip of the articulated jaw 72, the input torque to the leadscrew 82 is approximately 0.2 N m and the leadscrew 82 has 29 turns.

The leadscrew actuation mechanism can be fabricated using available materials and components. For example, many components of the leadscrew actuation mechanism can be fabricated from an available stainless steel(s). The leadscrew driven cam 84 can be coated (e.g., TiN) to reduce friction against the surfaces it rubs against (e.g., leadscrew 82; end effector base 74; proximal sides 100, 102 of the articulated jaw 72). Stranded cables can be used to drive the first actuation mechanism.

FIGS. 8A through 8F illustrate components of a cable actuation mechanism 110, in accordance with many embodiments. As described above, the leadscrew driven cam 84 can be positioned at the distal end of the cam slot 86 (i.e., near the pivot pin 88). For such a distal position of the leadscrew driven cam 84, as discussed above, the rotational position of the articulated jaw 72 about the pivot pin 88 is unconstrained for a range of rotational positions of the articulated jaw 72. Accordingly, the rotational position of the articulated jaw 72 about the pivot pin 88 can be controlled by the cable actuation mechanism 110. The cable actuation mechanism 110 is operable to vary the rotational position of the articulated jaw between the clamped configuration and the open configuration. The cable actuation mechanism 110 includes a pair of pull cables 112, 114. The cable actuation mechanism 110 also includes a first linkage 116 that is used to rotate the articulated jaw 72 about the pivot pin 88 towards the clamped configuration, and an analogous second linkage 118 that is used to rotate the articulated jaw 72 about the pivot pin 88 towards the open configuration. The first linkage 116 (shown in FIGS. 8A and 8B) includes a rotary link 120 that is mounted for rotation relative to the end effector base 74 via a pivot pin 122. A connecting link 124 couples the rotary link 120 to the articulated jaw 72 via a pivot pin 126 and a pivot pin 128. The first linkage 116 is articulated via a pulling motion of the pull cable 112. In operation, a pulling motion of the pull cable 112 rotates the rotary link 120 in a clockwise direction about the pivot pin 122. The resulting motion of the connecting link 124 rotates the articulated jaw 72 in a counter-clockwise direction about the pivot pin 88 towards the clamped configuration.

The second linkage 118 (shown in FIGS. 8C through 8F) of the cable actuation mechanism 110 includes analogous components to the first linkage 116, for example, a rotary link 130 mounted for rotation relative to the end effector base 74 via a pivot pin 132, and a connecting link 134 that couples the rotary link 130 to the articulated jaw 72 via two pivot pins 136, 138. The second linkage 118 is articulated via a pulling motion of the pull cable 114. The second linkage 118 is configured such that a pulling motion of the pull cable 114 rotates the articulated jaw 72 about the pivot pin 88 towards the open configuration. In many embodiments, the pivot pin 136 between the connecting link 134 and the rotary link 130 of the second linkage 118 is 180 degrees out of phase with the pivot pin 126 between the connecting link 124 and the rotary link 120 of the first linkage 116. Coordinated pulling and extension of the pull cables 112, 114 of the cable actuation mechanism 110 is used to articulate the articulated jaw 72 between the open and clamped configurations. In order to best provide equal and opposite cable motion (and thereby maintain cable tension in a capstan-driven system described below), a common rotational axis for the pivot pins 122, 132 is configured to lie on a plane that contains the rotational axes for pivot pins 128, 138 when the articulated jaw 72 is closed (or nearly closed) and again when the when the articulated jaw 72 is open (or nearly open). The connecting links 124, 134 are assembled symmetrically opposite about this same plane for the first and second linkages 116, 118. The distance between the pivot pins 122, 126 and between the pivot pins 132, 136 is the same for both the first and second linkages 116, 118, and the distance between the pivot pins 126, 128 and between the pivot pins 136, 138 is the same for both the first and second linkages 116, 118.

Figure 9A:
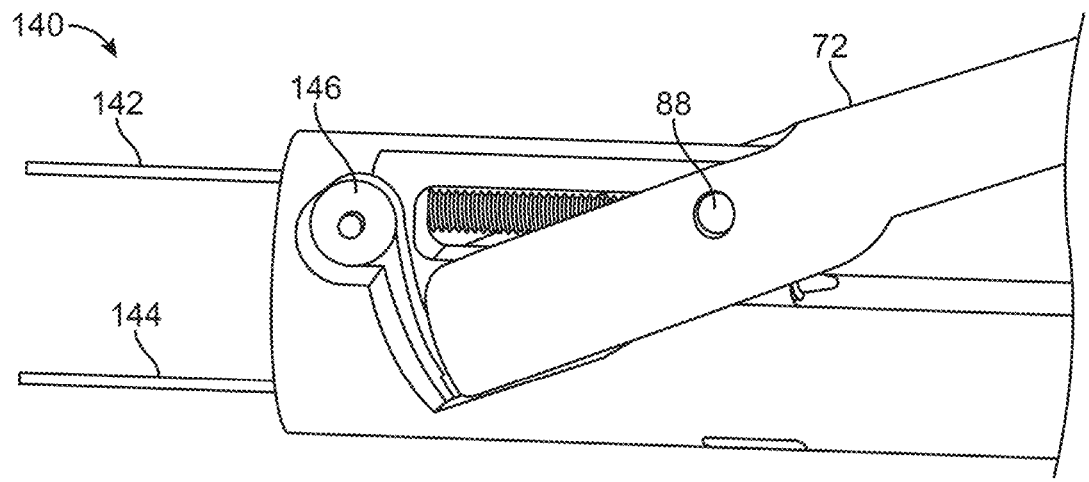
FIG. 9A is a perspective view illustrating a cable actuation mechanism, showing a cable used to articulate the jaw towards a clamped configuration, in accordance with many embodiments.
Figure 9B:
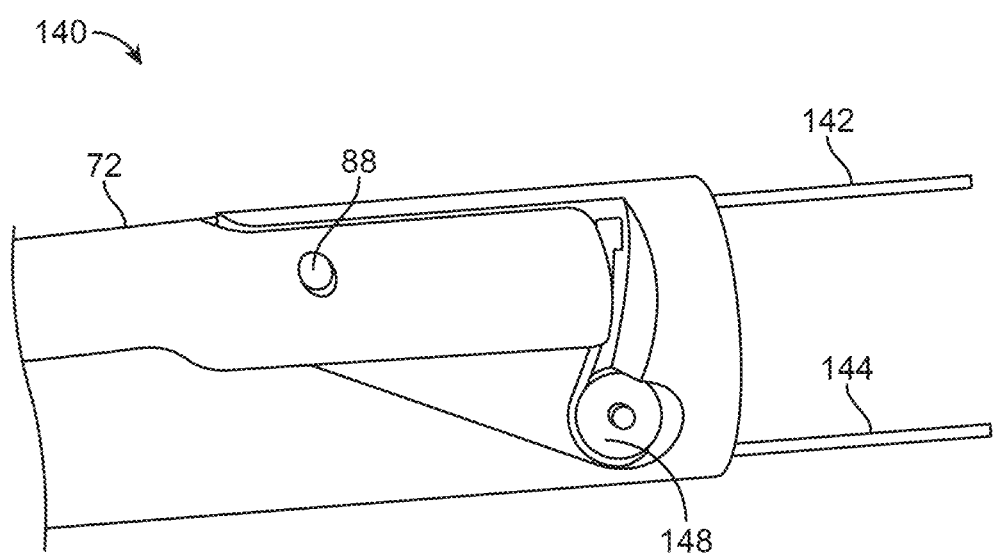
FIG. 9B is a perspective view illustrating the cable actuation mechanism of FIG. 9A, showing a cable used to articulate the jaw towards an open configuration.

FIGS. 9A and 9B illustrate an articulation of the articulated jaw 72 via another cable actuation mechanism 140, in accordance with many embodiments. In embodiment 140 of the cable actuation mechanism, a first pull cable 142 and a second pull cable 144 are directly coupled with the proximal end of the articulated jaw 72. The first pull cable 142 wraps around a first pulley 146 so that a pulling motion of the first pull cable 142 rotates the articulated jaw 72 about the pivot pin 88 towards the clamped configuration. The second pull cable 144 wraps around a second pulley 148 so that a pulling motion of the second pull cable 144 rotates the articulated jaw 72 about the pivot pin 88 towards the open configuration. Accordingly, coordinated pulling and extension of the first and second pull cables of the cable actuation mechanism 140 is used to articulate the articulated jaw 72 between the open and clamped configurations. In order to best provide equal and opposite cable motion (and thereby maintain cable tension in the capstan-driven system described below), the radius of the arc prescribed by cable 142 about the pivot 88 is substantially the same as the radius prescribed by cable 144 about the pivot 88.

In many embodiments, the cable (i.e., low force) actuation mechanism comprises a pair of pull cables that are actuated via an actuation feature disposed in a proximal tool chassis. The proximal tool chassis can be configured to be releasably mountable to a robotic tool manipulator having a drive mechanism that operatively couples with the actuation feature. For example, the pair of pull cables can be wrapped around a capstan located in the proximal tool chassis. The capstan can be operatively coupled with a capstan drive servo motor of the robotic tool manipulator when the proximal tool chassis is mounted to the robotic tool manipulator. Selective rotation of the capstan drive motor can be used to produce a corresponding rotation of the capstan. Rotation of the capstan can be used to produce a coordinated extension and retraction of the pull cables. As discussed above, coordinated actuation of the pull cables can be used to produce a corresponding articulation of the articulated jaw of the end effector.

In many embodiments, the fast response/low force mode is provided by a cable actuation mechanism that is back-drivable. For example, an external force applied to the articulated jaw can be used to rotate the articulated jaw towards the clamped configuration and back-drive the cable actuation mechanism. With a cable actuation mechanism that comprises a pair of pull cables wrapped around a capstan, an external force that rotates the articulated jaw towards the clamped configuration produces an increase in tension in one of the pull cables and a decrease in tension in the other pull cable, thereby causing the capstan to rotate in response. As is known, such a cable driven system can be configured to have sufficient efficiency for back-drivability. Likewise, an external force applied to the articulated jaw can be used to rotate the articulated jaw towards the open configuration and back-drive the cable actuation mechanism. As discussed above, a back-drivable fast response/low force actuation mechanism provides a number of benefits.

Alternate mechanisms can be used to provide a fast response/low force articulation mode. For example, an actuation mechanism comprising push/pull rods can be used.

Figure 10:
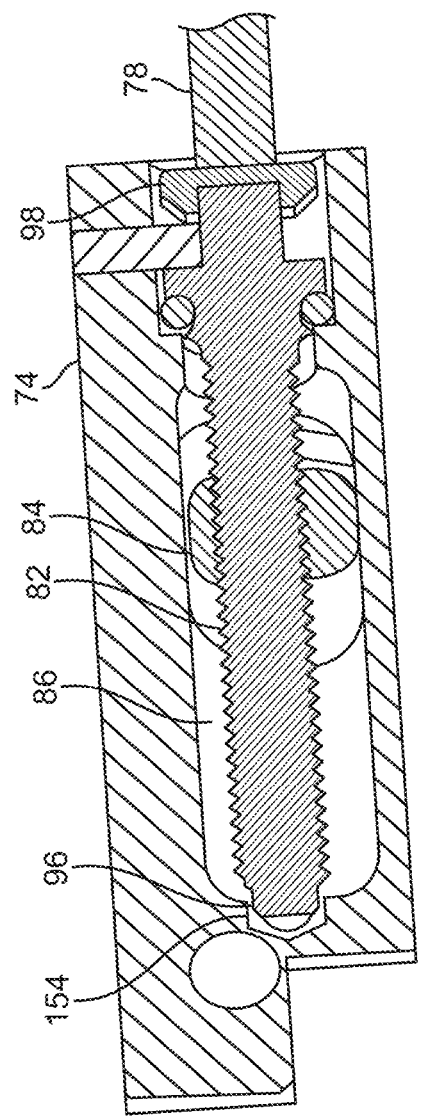
FIG. 10 is a cross-sectional view illustrating components of a leadscrew actuation mechanism, in accordance with many embodiments.

FIG. 10 is a cross-sectional view illustrating components of the above discussed leadscrew actuation mechanism. The illustrated components include the leadscrew 82, the leadscrew driven cam 84, the cam slot 86 in the end effector base 74, the distal journal surface 96, the cylindrical receptacle 154 in the end effector base, and the proximal bearing 98 supported by the end effector base 74.

Figure 11:
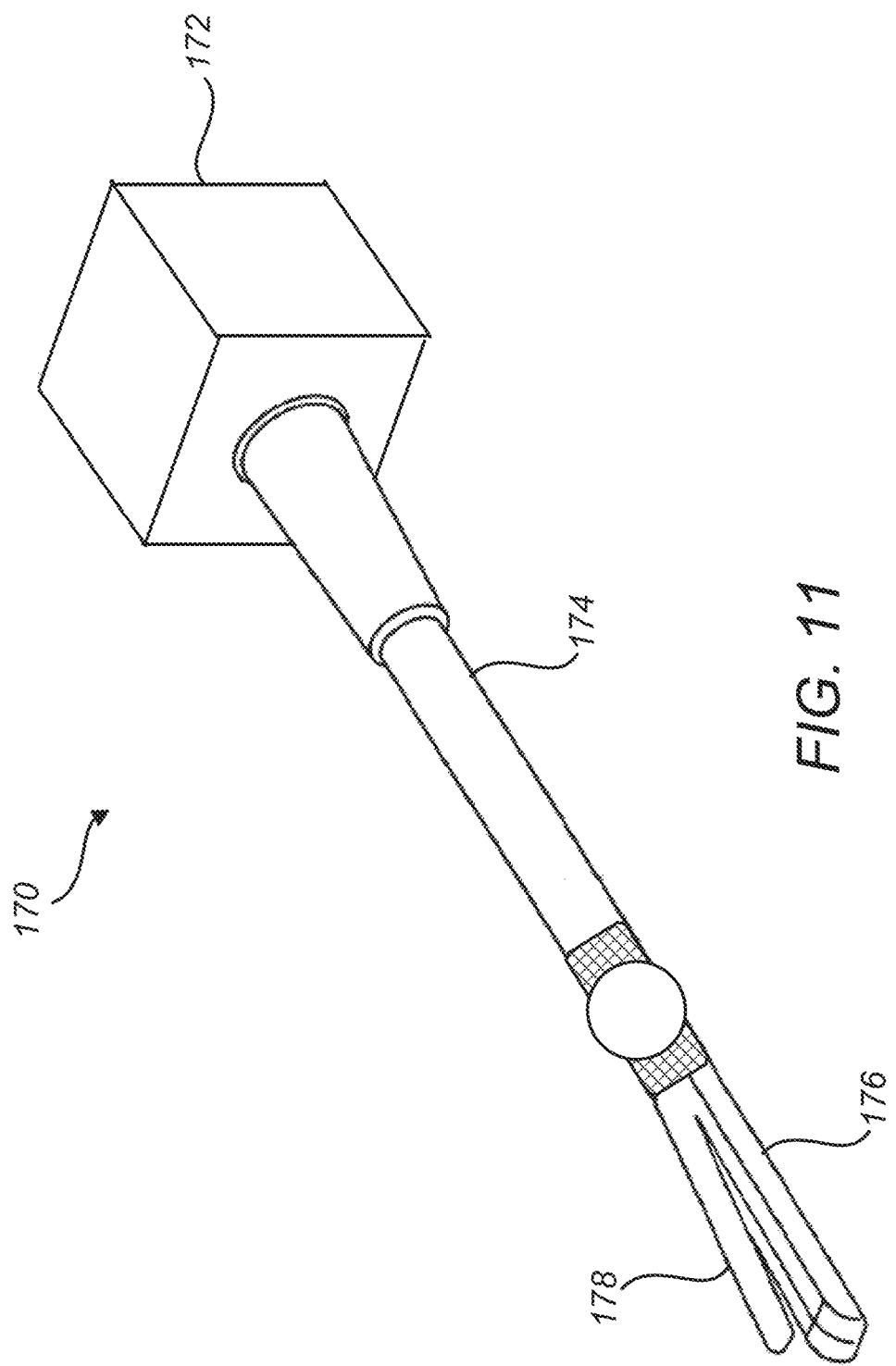
FIG. 11 is a simplified diagrammatic illustration of a tool assembly, in accordance with many embodiments.

FIG. 11 is a simplified perspective view diagrammatic illustration of a tool assembly 170, in accordance with many embodiments. The tool assembly 170 includes a proximal actuation mechanism 172, an elongate shaft 174 having a proximal end and a distal end, a tool body 176 disposed at the distal end of the shaft, a jaw 178 movable relative to the tool body 176 between a clamped configuration and an open configuration, a first actuation mechanism coupled with the jaw, and a second actuation mechanism coupled with the jaw. The first actuation mechanism is operable to vary the position of the jaw relative to the tool body between the clamped configuration and the open configuration. The second actuation mechanism has a first configuration where the jaw is held in the clamped configuration and a second configuration where the position of the jaw relative to the tool body is unconstrained by the second actuation mechanism. The first actuation mechanism is operatively coupled with the proximal actuation mechanism. In many embodiments, the first actuation mechanism comprises a pair of pull cables that are actuated by the proximal actuation mechanism. The second actuation mechanism is operatively coupled with the proximal actuation mechanism. In many embodiments, the second actuation mechanism includes a leadscrew driven cam located in the tool body that is driven by the proximal actuation mechanism via a drive shaft extending through the elongate shaft 174 from the proximal actuation mechanism.

The tool assembly 170 can be configured for use in a variety of applications. For example, the tool assembly 170 can be configured as a hand held device with manual and/or automated actuation used in the proximal actuation mechanism. The tool assembly 170 can also be configured for use in surgical applications, for example, electrocautery sealing, stapling, etc. The tool assembly 170 can have applications beyond minimally invasive robotic surgery, for example, non-robotic minimally invasive surgery, non-minimally invasive robotic surgery, non-robotic non-minimally invasive surgery, as well as other applications where the use of the disclosed redundant jaw actuation would be beneficial.

Figure 12:
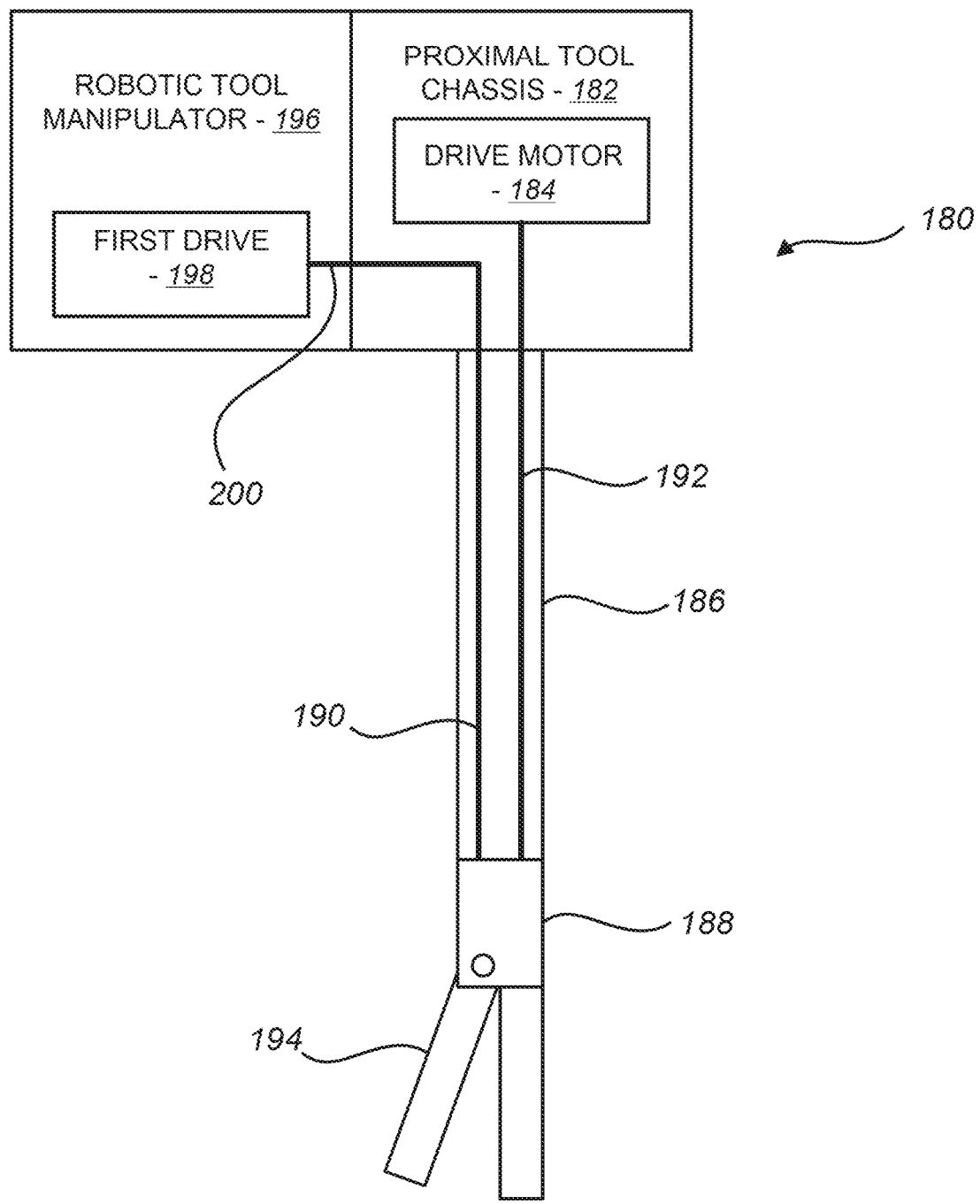
FIG. 12 is a simplified diagrammatic illustration of a robotic tool mounted to a robotic tool manipulator, in accordance with many embodiments.

Redundant jaw actuation can be used to articulate a jaw of a robotic tool end effector. For example, FIG. 12 schematically illustrates a robotic tool 180 employing redundant jaw actuation. The robotic tool 180 includes a proximal tool chassis 182, a drive motor 184, an instrument shaft 186, a distal end effector 188, a first actuation mechanism portion 190, and a second actuation mechanism 192. The distal end effector 188 comprises an articulated jaw 194. The proximal tool chassis 182 is releasably mountable to a robotic tool manipulator 196 having a first drive 198, and a first actuation mechanism portion 200 that operatively couples with the first actuation mechanism portion 190 of the robotic tool 180 when the proximal tool chassis 182 is mounted to the robotic tool manipulator 196. The instrument shaft 186 has a proximal end adjacent the tool chassis 182, and a distal end adjacent the end effector 188. The first actuation mechanism (comprising portion 200 and portion 190) couples the first drive 198 to the articulated jaw 194 when the tool chassis 182 is mounted to the tool manipulator 196 so as to articulate the end effector 188 between an open configuration and a clamped configuration. The second actuation mechanism 192 couples the drive motor 184 to the articulated jaw 194 so as to articulate the end effector into the clamped configuration from the open configuration. The first actuation mechanism can be a cable actuation mechanism, for example, an above discussed cable actuation mechanism that provides the fast response/low force mode. In many embodiments, the first actuation mechanism is back-drivable. The second actuation mechanism can include a drive shaft that couples the drive motor 184 with a leadscrew actuation mechanism, for example, an above discussed leadscrew actuation mechanism that provides the high clamping force mode. In many embodiments, the second actuation mechanism is non-back-drivable.

It is understood that the examples and embodiments described herein are for illustrative purposes and that various modifications or changes in light thereof will be suggested to persons skilled in the art and are to be included within the spirit and purview of this application and the scope of the appended claims. Numerous different combinations are possible, and such combinations are considered to be part of the present invention.

What is claimed is:

1. A surgical instrument comprising:
   an end effector comprising an end effector base and an articulated jaw rotatably mounted to the end effector base for rotation of the articulated jaw relative to the end effector base around an articulated jaw pivot axis that is fixed relative to the end effector base, wherein the end effector base comprises an opposing jaw; and
   a first actuation mechanism comprising a first pulley and a first cable segment,
   wherein the first pulley is mounted for rotation relative to the end effector base,
   wherein the first cable segment is interfaced with a sector of the first pulley,
   wherein the first cable segment has a distal end that is attached to the articulated jaw, and
   wherein the first actuation mechanism is operable to retract the first cable segment to cause the articulated jaw to apply a grasping force to a tissue disposed between the articulated jaw and the opposing jaw.

2. The surgical instrument of claim 1, wherein the first actuation mechanism is back-drivable.

3. The surgical instrument of claim 1, further comprising a second actuation mechanism operable to cause the articulated jaw to apply a clamping force to the tissue having a magnitude that exceeds any magnitude of the grasping force that can be applied to the tissue via the first actuation mechanism.

4. The surgical instrument of claim 3, wherein the clamping force is at least 20 lbs.

5. The surgical instrument of claim 3, wherein the second actuation mechanism is non-back-drivable.

6. The surgical instrument of claim 3, wherein the second actuation mechanism has a first configuration for applying the clamping force to the tissue and a second configuration in which the articulated jaw is not constrained by the second actuation mechanism.

7. The surgical instrument of claim 3, wherein:
   the second actuation mechanism comprises a leadscrew and a leadscrew driven cam drivingly coupled to the leadscrew; and
   the second actuation mechanism is operable to rotate the leadscrew to reposition the leadscrew driven cam along the leadscrew so as to cause the articulated jaw to apply the clamping force to the tissue disposed between the articulated jaw and the opposing jaw.

8. The surgical instrument of claim 7, further comprising a drive shaft rotationally coupled with the leadscrew.

9. The surgical instrument of claim 7, wherein the leadscrew driven cam is configured to be controllably interfaced with a proximal portion of the articulated jaw disposed proximal to the articulated jaw pivot axis.

10. The surgical instrument of claim 3, comprising a treatment device operable to perform a surgical task to the tissue disposed between the articulated jaw and the opposing jaw, wherein the treatment device comprises the opposing jaw.

11. The surgical instrument of claim 10, comprising a treatment device drive shaft drivingly coupled with the treatment device.

12. The surgical instrument of claim 11, wherein the treatment device comprises a stapling device.

13. The surgical instrument of claim 12, wherein the stapling device comprises a leadscrew rotated via rotation of the treatment device drive shaft.

14. The surgical instrument of claim 1, further comprising a treatment device and a drive shaft, wherein:
the end effector comprises the treatment device; and
the drive shaft is drivingly coupled with the treatment device.

15. The surgical instrument of claim 1, further comprising a stapling device and a drive shaft, wherein:
the end effector comprises the stapling device; and
the drive shaft is drivingly coupled with the stapling device.

16. A surgical instrument comprising:
an end effector comprising an end effector base and an articulated jaw rotatably mounted to the end effector base for rotation of the articulated jaw relative to the end effector base around an articulated jaw pivot axis that is fixed relative to the end effector base, wherein the end effector base comprises an opposing jaw; and
an actuation mechanism comprising a first rotary link, a first connecting link, and a first cable segment, wherein:
the first rotary link is mounted for rotation relative to the end effector base;
the first connecting link is pivotally coupled to the first rotary link;
the first connecting link is pivotally coupled to the articulated jaw;
the first cable segment is drivingly coupled to the first rotary link; and
the actuation mechanism is operable to retract the first cable segment to rotate the first rotary link relative to the end effector base to cause the articulated jaw to apply a grasping force to a tissue disposed between the articulated jaw and the opposing jaw.

17. The surgical instrument of claim 16, wherein:
the actuation mechanism comprises a second rotary link, a second connecting link, and a second cable segment;
the second rotary link is mounted for rotation relative to the end effector base;
the second connecting link is pivotally coupled to the second rotary link;
the second connecting link is pivotally coupled to the articulated jaw;
the second cable segment is drivingly coupled to the second rotary link; and
the actuation mechanism is operable to retract the second cable segment to rotate the second rotary link relative to the end effector base to cause the articulated jaw to reorient the articulated jaw relative to the opposing jaw from a closed jaw configuration to an open jaw configuration.

18. The surgical instrument of claim 17, wherein:
the first cable segment has a first cable segment distal end that is fixedly attached to the first rotary link; and
the second cable segment has a second cable segment distal end that is fixedly attached to the second rotary link.

19. The surgical instrument of claim 16, further comprising a treatment device and a drive shaft, wherein:
the end effector comprises the treatment device; and
the drive shaft is drivingly coupled with the treatment device.

20. The surgical instrument of claim 16, further comprising a stapling device and a drive shaft, wherein:
the end effector comprises the stapling device; and
the drive shaft is drivingly coupled with the stapling device.

* * * * *